(12) United States Patent
Berger et al.

(10) Patent No.: US 10,813,911 B2
(45) Date of Patent: Oct. 27, 2020

(54) METHODS OF TREATING AND/OR PREVENTING CHRONIC OBSTRUCTIVE PULMONARY DISEASE

(71) Applicants: UNIVERSITE DE BORDEAUX, Bordeaux (FR); INSTITUT NATIONAL DE LA SANTE ET DE LA RECHERCHE MEDICALE, Paris (FR); CENTRE HOSPITALIER UNIVERSITAIRE DE BORDEAUX, Talence (FR)

(72) Inventors: Patrick Berger, Bordeaux (FR); Isabelle Dupin, Talence (FR); Pierre-Olivier Girodet, Bordeaux (FR)

(*) Notice: Subject to any disclaimer, the term of this patent is extended or adjusted under 35 U.S.C. 154(b) by 274 days.

(21) Appl. No.: 15/547,099

(22) PCT Filed: Jan. 28, 2016

(86) PCT No.: PCT/EP2016/051771
§ 371 (c)(1),
(2) Date: Jul. 28, 2017

(87) PCT Pub. No.: WO2016/120369
PCT Pub. Date: Aug. 4, 2016

(65) Prior Publication Data
US 2018/0271831 A1    Sep. 27, 2018

(30) Foreign Application Priority Data

Jan. 28, 2015    (EP) .................................... 5152886

(51) Int. Cl.
*A61K 31/395*    (2006.01)
*A61K 45/06*     (2006.01)
(Continued)

(52) U.S. Cl.
CPC .......... *A61K 31/395* (2013.01); *A61K 9/0075* (2013.01); *A61K 31/198* (2013.01);
(Continued)

(58) Field of Classification Search
None
See application file for complete search history.

(56) References Cited

U.S. PATENT DOCUMENTS

2012/0088769 A1    4/2012    Ly

FOREIGN PATENT DOCUMENTS

| WO | 2009/074807 A2 | 6/2009 |
| WO | 2013052844 | 4/2013 |
| WO | 2014132100 | 9/2014 |

OTHER PUBLICATIONS

ClincialTrials.Gov, To assess the safety and continuous IV administration of plerixafor in patients with advanced pancreatic, ovarian and colorectal cancers, Retrieved online: <URL-https://clinicaltrials.gov/ct2/history/NCT02179970?V_2=View#StudyPageTop>. Retrieved Jun. 20, 2019, Aug. 8, 2014.*

(Continued)

*Primary Examiner* — Claire Kaufman
(74) *Attorney, Agent, or Firm* — Law Offices of Albert Wai-Kit Chan, PLLC

(57) ABSTRACT

The present invention relates to a novel composition or method of use for the treatment and/or the prevention of chronic obstructive pulmonary disease (COPD) and acute exacerbations of chronic obstructive pulmonary disease (AECOPDs).

11 Claims, 12 Drawing Sheets

Specification includes a Sequence Listing.

(51) Int. Cl.
A61K 31/198 (2006.01)
A61K 31/496 (2006.01)
A61P 11/00 (2006.01)
A61K 9/00 (2006.01)

(52) U.S. Cl.
CPC ............ *A61K 31/496* (2013.01); *A61K 45/06* (2013.01); *A61P 11/00* (2018.01); *G01N 2333/7158* (2013.01); *G01N 2800/122* (2013.01); *G01N 2800/50* (2013.01); *G01N 2800/52* (2013.01)

(56) References Cited

OTHER PUBLICATIONS

Fruehauf, S., Current clinical indications for plerixafor, Transfus. Med. Hemother. 40-246-250, Jul. 19, 2013.*
Bendall et al., New therapeis targeting chemokine receptors: can changing the way cells traffic be used to treat human disease? Curr. Topics Memb. 55:331-365, 2005, pp. 331 and 337 only.*
Phillips et al.,Circulating fibrocytes traffice to the lungs in response to CXCL12 and mediate fibrosis, J. Clin. Invest. 114(3):438-446, 2004.*
Geribaldi et al., Regulatory T cells reduce acute lung injury fibroproliferation by decraseing fibrocyte recruitment, Am. J. Resp. Cell Mol. Biol. 48(1):35-43, Jan. 2013.*
Debnath et al., Small molecule inhibitors of CXCR4, Theranostics, 3(1):47-75, 2013.*
Cao et al., Effect of low-dose ritonavir on the pharmacokinetics of the CXCR4 antagonist AMD070 in healthy volunteers, Antimicrob. Agents Chemo., 52(5):1630-1634, May 2008.*
Kim et al.,CXCR4 signaling regulates metastasis of chemoresistant melanoma cells by a lymphatic metastatic niche, Canc. Res. 70(2): 10411-10421, 2010.*
Tamamura et al., Identification of a CXCR4 antagonist, a T140 analog, as an anti-rheumatoid arthritis agent, FEBS Lett. 569:99-104, 2004.*
Jacobson et al., CXCR4 chemokine receptor overview: biology, pathology and applications in imaging and therapy, Theranostics, 3(1):1-2, 2013.*
Brown, W.M., Treating COPD with PDE 4 inhibitors, Intl. J. COPD, 2(4):517-533, 2007.*
Miravitlles et al., Treatment of COPD by clinical phenotypes: putting old evidence into clinical practice, Eur. Respir. J. 41:1252-1256, 2012.*
Mehad et al., Fibrocyte CXCR4 regulation as a therapeutic target in pulmonary fibrosis, Int. J. Biochem. Cell Biol. 41:1708-1718, 2009.*
Murray, LA, Commonalities between the pro-fibrotic mechanisms in COPD and IPF, Pulm. Pharmacol. Therapeutics, 25:276-280, 2012.*
Kaddah et al., Circulating fibrocytes are an indicator of severity and exacerbation in chronic obstructive pulmonary disease, Egypt. J. Chest Dis. Tuerberculosis, 63:805-813, 2014.*
Barnes, P.J., Small airway fibrosis in COPD, Intl. J. Biochem. Cell Biol. 116:105598, pp. 1-3, 2019.*
Tanner et al., Animal modles reflecting chronic obstructive pulmonary disease and related respiratory disorders: translating preclinical data into clincial relevance, J. Innate Immun. 12:203-225, 2020.*
International Search Report, dated Mar. 10, 2016, for International Application No. PCT/EP2016/051771.
Written Opinion, dated Aug. 4, 2016, for International Application No. PCT/EP2016/051771.
Partial European Search Report, dated May 19, 2015, for European Application EP 15152886.
European Search Report, dated Oct. 9, 2015, for European Application EP 15152886.
2013, "AstraZeneca AZD2423 Mechanism of Action", https://ncats.nih.gov/files/AZD2423.pdf.
International Preliminary Report on Patentability, dated Aug. 1, 2017, for International Application No. PCT/EP2016/051771.
Barnes et. al., "COPD: current therapeutic interventions and future approaches", Eur Respir J 2005; 25: 1084-11106 [https://doi.org/10.1183/09031936.05.00139104].
Cazzola et al,. "Emerging anti-inflammatory strategies for COPD", Eur Respir J 2012; 40: 724-741 [https://doi.org/10.1183/09031936.00213711].
Watz, H., "Next generation of anti-inflammatory therapy for COPD?", Eur Respir J 2017; 50: 1702084 [https://doi.org/10.1183/13993003.02084-2017].
Japanese Office Action, dated Nov. 7, 2019, for UNIVERSITE DE BORDEAUX et al., Japanese Application No. 2017-540788.
Song et al., 2010, "Inhibitory Effect of CXC chemokine receptor 4 antagonist AMD3100 on bleomycin induced murine pulmonary fibrosis", Experimental and Molecular Medicine, vol. 42, No. 6, pp. 465-476.
Wang et al., 2014, "Hydroxysafflor Yellow A Attenuates Small Airway Remodeling in a Rat Model of Chronic Obstructive Pulmonary Disease", Biological and Pharmaceutical Bulletin, vol. 37, No. 10. pp. 1591-1598.
Indian Office Action, dated Nov. 26, 2019, for UNIVERSITE DE BORDEAUX et al., Indian Application No. 201717027493, filed Aug. 2, 2017.
Chinese Office Action, dated Dec. 12, 2019, for UNIVERSITE DE BORDEAUX et al., Chinese Application No. 201680008472.9.
Australian Office Action, dated Jan. 24, 2020, for UNIVERSITE DE BORDEAUX et al., Australian Application No. 2016212067.

* cited by examiner

SEQUENCE LISTING

<160> NUMBER OF SEQ ID NOS: 10

<210> SEQ ID NO 1
<211> LENGTH: 7
<212> TYPE: PRT
<213> ORGANISM: human

<400> SEQUENCE: 1

Leu Gly Thr Phe Leu Lys Cys
1               5

<210> SEQ ID NO 2
<211> LENGTH: 5
<212> TYPE: PRT
<213> ORGANISM: human

<400> SEQUENCE: 2

Leu Phe Thr Lys Cys
1               5

<210> SEQ ID NO 3
<211> LENGTH: 5
<212> TYPE: PRT
<213> ORGANISM: human

<400> SEQUENCE: 3

Cys Lys Thr Phe Leu
1               5

<210> SEQ ID NO 4
<211> LENGTH: 7
<212> TYPE: PRT
<213> ORGANISM: human

<400> SEQUENCE: 4

His Thr Leu Met Arg Asn Leu
1               5

<210> SEQ ID NO 5
<211> LENGTH: 7
<212> TYPE: PRT
<213> ORGANISM: human

<400> SEQUENCE: 5

Leu Asn Arg Met Leu Thr His
1               5

<210> SEQ ID NO 6
<211> LENGTH: 7
<212> TYPE: PRT
<213> ORGANISM: human

<400> SEQUENCE: 6

Leu Asn Thr Phe Gln Glu Phe
1               5

<210> SEQ ID NO 7
<211> LENGTH: 7
<212> TYPE: PRT
<213> ORGANISM: human

<400> SEQUENCE: 7

Phe Glu Gln Phe Thr Asn Leu
1               5

```
<210> SEQ ID NO 8
<211> LENGTH: 4
<212> TYPE: PRT
<213> ORGANISM: human

<400> SEQUENCE: 8

Thr Phe Leu Lys
1

<210> SEQ ID NO 9
<211> LENGTH: 8
<212> TYPE: PRT
<213> ORGANISM: human

<400> SEQUENCE: 9

Cys Pro Trp Tyr Phe Trp Pro Cys
1               5

<210> SEQ ID NO 10
<211> LENGTH: 5
<212> TYPE: PRT
<213> ORGANISM: human

<400> SEQUENCE: 10

Gly Asp Tyr Arg Arg
1               5
```

METHODS OF TREATING AND/OR PREVENTING CHRONIC OBSTRUCTIVE PULMONARY DISEASE

CROSS-REFERENCE TO RELATED APPLICATIONS

This application is a National Stage of Int'l App'l No. PCT/EP2016/051771, filed Jan. 28, 2016, which claims the benefit of European application No. 15152886.6, filed Jan. 28, 2015. The entire contents and disclosures of the preceding applications are hereby incorporated by reference into this application.

FIELD OF INVENTION

The invention relates to novel compositions and methods for the prevention and/or treatment of chronic obstructive pulmonary disease (COPD) and acute exacerbations of chronic obstructive pulmonary disease (AECOPDs).

BACKGROUND OF THE INVENTION

COPD is a very frequent airway disease that affects more than 200 million people worldwide. It is currently the fourth leading cause of death, but the mortality may reach the third cause of death in 2020. It is characterized by persistent airflow limitation that is usually progressive and associated with an enhanced chronic inflammatory response in the airways and the lung to noxious particles or gases. The main risk factor for COPD is tobacco smoking. The disease is characterized by chronic bronchial inflammation and remodeling of distal airways, and in particular a bronchial and peri-bronchial fibrosis, leading to persistent airflow limitation.

Exacerbations and co-morbidities contribute to the overall severity in individual patients. There are several anatomic lesions that contribute to the reduced airflow found in COPD patients. These include accumulation of mucous secretions, peri-bronchiolar fibrosis, narrowing of small airways and destruction of alveolar walls, which is the defining characteristic of emphysema. The chronic course of COPD is also frequently worsened by acute exacerbations (AECOPDs), most often related to viral or bacterial infections. These AECOPDs are associated with a burst of neutrophilic and sometimes eosinophilic inflammation. AECOPDs affect nearly 80% of COPD patients over a 3 year-period and the frequency of exacerbation is mainly related with the presence of previous exacerbations.

AECOPDs result in enormous healthcare costs, especially related to hospitalisations. AECOPDs dramatically affect the quality of life and play a role in the worsening of the disease: lung function declines more rapidly in patients with frequent exacerbations, with an increased risk of death. In particular, a high mortality rate has been reported in COPD patients admitted to the hospital for AECOPDs, and reached up to 45% within the 4 subsequent years. Severe AECOPDs are considered as an independent prognostic factor of mortality. However, the mechanisms of these latter findings remain totally unknown.

Current pharmacologic treatments act on symptoms and quality of life but do not improve mortality or the natural history of the disease, with the latter being characterized by a more rapid decrease in lung function.

To date the recruitment of fibrocytes during and following an AECOPD had not been investigated, and little is known about the role of modulating fibrocytes and ensuing effect on disease progression. Applicants investigated recruitment and migration of peripheral blood fibrocytes in patients during COPD exacerbations and understood the need for developing new therapies around of this concept. In particular, Applicants showed that fibrocytes expressing CXCR4, CCR3, and CCR2, the chemokine receptor for CXCL12, CCL11, CCL7, CCL13 and CCL2, was significantly increased in patients during AECOPDs, and that these specific fibrocytes were highly correlated to mortality and low lung function. Applicants have successfully identified a novel drug discovery pathway and new drugs for the treatment and/or the prevention of COPD and AECOPDs by showing that antagonists of CCR2/CCL2, CCR2/CCL7, CCR2/CCL13, CXCR4/CXCL12, and/or CCR3/CCL11 receptor/ligand pairs are useful for the treatment and/or prevention of COPD and AECOPDs in preventing fibrocytes recruitment/migration in patients during AECOPDs.

SUMMARY OF THE INVENTION

The present invention thus provides a composition for use in a method for preventing and/or treating COPD and AECOPDs comprising a therapeutically effective amount of at least one antagonist or inhibitor of chemokine receptor CXCR4, CCR2, and/or CCR3, variants and/or isoforms, ligands thereof, their variants and/or isoforms thereof. Antagonists of CCR2/CCL2, CCR2/CCL7, CCR2/CCL13, CXCR4/CXCL12, and/or CCR3/CCL11 receptor/ligand pairs may be chosen among small organic or synthetic molecules, natural products, peptides, proteins, peptidomimetics, polyclonal or monoclonal antibodies, antibody fragments, nucleic acid agents, e.g., RNAi, siRNA, shRNAs, an antisense, a ribozyme, or a DNAzyme.

The present invention is also directed to a method of treating and/or preventing COPD and/or AECOPDs, as well as to a method of suppressing fibrocytes recruitment and migration mediated and/or modulated by CCR2 and/or CCR3 and/or CXCR4 in a subject having COPD, or AECOPDs or at a risk of developing COPD or AECOPDs, comprising administering to the subject a therapeutically effective amount of at least one antagonist of CCR2/CCL2, CCR2/CCL7, CCR2/CCL13, CXCR4/CXCL12, and/or CCR3/CCL11 receptor/ligand pairs, variants, and/or isoforms thereof.

The present invention is further directed to the use of a therapeutically effective amount of at least one antagonist or inhibitor of chemokine receptor CXCR4, CCR2, and/or CCR3, and/or variants and/or isoforms, ligands thereof, or the use of a therapeutically effective amount of at least one antagonist of CCR2/CCL2, CCR2/CCL7, CCR2/CCL13, CXCR4/CXCL12, and/or CCR3/CCL11 receptor/ligand pairs, variants, and/or isoforms thereof, for the preparation of a medicament for treating and/or preventing COPD and/or AECOPDs in a subject having COPD, or AECOPDs or at a risk of developing COPD or AECOPDs.

Preferred compositions and methods of use of the present invention relate to at least one antagonist or inhibitor of chemokine receptor CXCR4 and/or variants and/or isoforms, ligands thereof, and/or the use of one antagonist of CXCR4/CXCL12 receptor/ligand pair, variants, and/or isoforms thereof.

The present invention further provides novel markers for COPD disease development and progression, for AECOPDs and drug discovery targets.

The present invention still further provides in vitro or in vivo methods of screening or identifying antagonist agents as well as in vitro method of measuring the level of at least one gene selected from the group consisting of CCR2, CCR3 and/or CXCR4 genes in the peripheral blood fibrocytes.

Finally, the present invention is directed to a method of assessing the risk of COPD or AECOPDs in a subject, comprising; a) obtaining a suitable sample from the said subject b) isolating and identifying the circulating fibrocytes in the said sample c) optionally assessing fibrocytes migration in the said sample and d) measuring the expression levels of CCR2 and/or CCR3 and/or CXCR4 chemokine receptors in the said sample. The present invention also provides a method for monitoring the response to a therapeutic agent in a patient suffering from COPD and AECOPDs, comprising the step of measuring the level of expression of at least one gene selected from the group consisting of CCR2, CCR3 and/ot CXCR4 gened in the peripheral blood fibrocytes of the patient.

DETAILED DESCRIPTION

Figure 1:
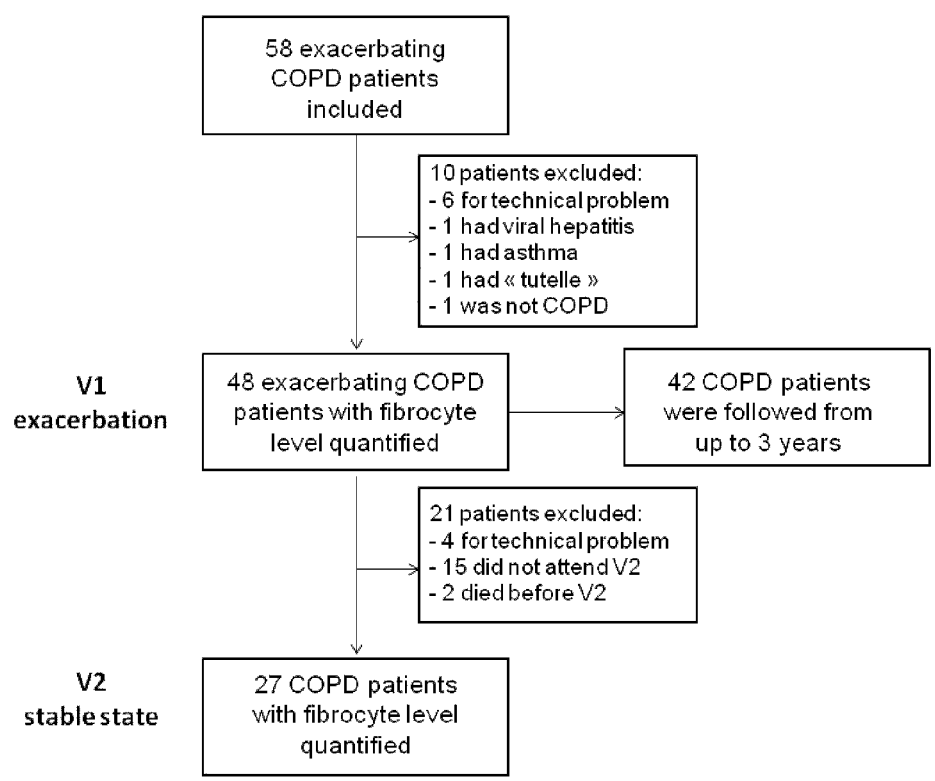
FIG. 1 shows the study design with the numbers of patients who were included and had their level of fibrocytes quantified.

Applicants investigated, in a translational clinical study, peripheral blood fibrocytes concentrations in COPD patients during an exacerbation and 2 months after the exacerbation at the stable state in comparison to control subjects and patients with non-exacerbating COPD. Furthermore, chemokine receptors were characterized, and migration properties of these fibrocytes from patients with COPD and control subjects were investigated.

Applicants have discovered a significant increased number of circulating fibrocytes in patients during AECOPDs as compared to control subjects, and that the number of circulating fibrocytes decreased in same patients two months after AECOPDs. Applicants demonstrated that a high percentage of circulating fibrocytes during exacerbations was associated with increased risk of death, and that the percentage of fibrocytes after AECOPDs was negatively correlated to several obstructive lung disease parameters, i.e., FEV1 (Forced expired in 1 second), FVC (Forced vital capacity), FEV1/FVC (Tiffeneau-Pinelli index), TLCO (Transfer lung capacity of carbon monoxide) and $PaO_2$ (Partial pressure of oxygen in arterial blood). In particular, Applicants discovered that fibrocytes expressed CXCR4, CCR2 and/or CCR3, the chemokine receptors for CXCL12, CCL2, CCL7, CCL13, and/or CCL11 chemokines, respectively.

Antagonists of chemokine receptors CXCR4, CCR2, and CCR3 decreased fibrocytes migration to plasma of exacerbating COPD patients, and thus were found to be useful according to the present invention for treating and/or preventing COPD and AECOPDs.

Preferred antagonists according to the invention, are antagonists of chemokine receptor CXCR4, such as, but without any limitations Plerixafor.

The present invention thus provides compounds, pharmaceutical compositions and methods of use of antagonists or inhibitors of CCR2/CCL2, CCR2/CCL7, CCR2/CCL13, CXCR4/CXCL12, and/or CCR3/CCL11 receptor/ligand pairs for use in the treatment and/or the prevention of COPD or AECOPDs. Preferred compounds according to the invention interfere with the binding of the native ligands to the CXCR4 receptor and inhibit activation of the receptor and subsequent downstream signalling pathways.

Chemokine receptor CXCR4 is meant C-X-C chemokine receptor type 4 (CXCR4). It is also known as fusin or cluster of differentiation 184 (CD184), which is a seven transmembrane (TM) G-protein coupled receptor (GPCR) belonging to Class I GPCR or rhodopsin-like GPCR family. The CXCR4 structure consists of 352 amino acid residues comprising an N-terminal domain, seven TM domains, three extra-cellular loops (ECL), three intra-cellular loops (ICL) and a C-terminal domain.

CXCR4 is specific for chemokine ligand 12 (CXCL12), which is also called stromal-derived-factor-1 (SDF-1). As a homeostatic chemokine, SDF-1 or CXCL12 is an 8 kDa chemokine peptide with 67 amino acid residues, mainly localized in bone marrow stromal cells. There are two different isoforms CXCL12-α and CXCL12-β. The amino acid sequence of human CXCL12-α or SDF-1α has GenBank accession number NP954637. The amino acid sequence of human CXCL12-β or SDF-1β has GenBank accession number NP000600. Human CXC12 is also described in U.S. Pat. Nos. 5,756,084 and 5,563,048.

Chemokine receptor CCR2 refers to the gene symbol approved by the HUGO Gene Nomenclature Committee for chemokine (C-C motif) receptor 2. The HGNC ID for this gene is 1603. The gene is located at chromosome position 3p21. The previous symbol and name for the gene is CMKBR2. Synonyms for this gene include CC-CKR-2, CD192, CKR2, FLJ78302, MCP-1-R. The NCBI Reference Sequence is NM001123041.2 Nucleic acid) and NP001116513.2 (amino acid). CCR2 is a receptor for CCL2, CCL7 and CCL13. The receptor mediates agonist-dependent calcium mobilization and inhibition of adenylyl cyclase. Two alternatively spliced transcript variants are expressed by the human CCR2 gene. The first variant (A) encodes a cytoplasmic isoform. It is alternatively spliced in the coding region resulting in a frameshift and use of a downstream stop codon, compared to variant B. All variants and isoforms are within the scope of the invention.

The chemokine (C-C motif) ligand 2 (CCL2) is also referred to as monocyte chemotactic protein 1 (MCP1) and small inducible cytokine A2. CCL2 is a small cytokine that belongs to the CC chemokine family. CCL2 recruits monocytes, memory T cells, and dendritic cells to the sites of inflammation produced by either tissue injury or infection.

CCL7 (monocyte chemoattractant protein-3, MCP-3) is a member of the CC-chemokine family (β-chemokines) characterized by two adjacent cysteine residues at the amino terminal of the mature protein. It is a ligand for CCR2 binding. The accession number of MCP-3 is X72308

Figure 3:
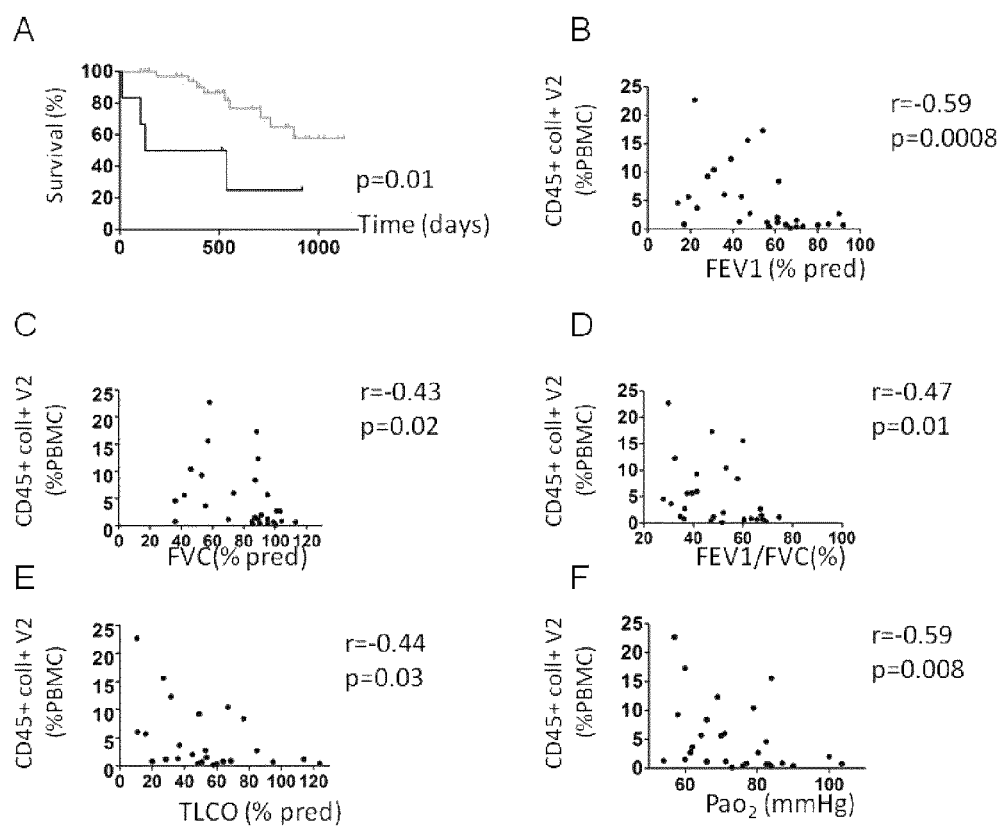
FIGS. 3A-F represent a Kaplan-Meier survival analysis of exacerbating COPD subjects, separated by the threshold percentage of CD45+ Coll+ cells in PBMC of 28 subjects measured at the time of exacerbation (V1). Of the 42 subjects with available survival data, 36 had values below (gray curve) and 6 above the threshold (black curve). Percentage of CD45+ Coll+ cells in PBMC as predictors of mortality in COPD subjects (A). B-F, Relationships between FEV1 (B), FVC (C), FEV1/CVF (D), TLCO (E), pO2 (F) and the percentage of CD45+ Coll+ cells in PBMC in exacerbating COPD patients at V2. FEV1: Forced Expiratory Volume in the 1st second; FVC: forced vital capacity; TLCO: carbon monoxide transfer factor; $Pao_2$: partial pressure of $O_2$ in arterial blood. Correlation coefficient (r) and significance level (p value) were obtained using non parametric Spearman analysis.

CCL13, also known as Monocyte Chemoattractant Protein-4 (MCP-4), is a CC chemokine that acts as a chemoattractant for monocytes, eosinophils and T cells and as an activator of basophils. It signals through the CCR2 and CCR3 receptors. Human MCP-4 (hMCP-4) sequence was first published in 1996. (Uguccioni et al., 1996, Monocyte Chemotactic Protein 4 (MCP-4), A Novel Structural and Functional Analogue of MCP-3 and Eotaxin, J. Exp. Med. 183:2379-2394). Human MCP-4 is a peptide of 8.6 kDa that consists of 75 amino acid residues. (FIG. 3.) It is also known as CK-β-10, SCY-A13 and NCC-1 (Swiss-Prot accession number Q99616) and was renamed CCL13 in the new chemokine nomenclature. (Zlotnik et al., 2000, Immunity, 12:121-127). CCL13 has the SWISSPROT accession no. Q99616; segment 34-58.

Chemokine receptor CCR3 refers to the gene symbol approved by the HUGO Gene Nomenclature Committee for chemokine (C-C motif) receptor 3. The HGNC ID for this gene is 1604. The gene is located at chromosome position 3p21 0.3. The previous symbol and name for the gene is CMKBR3. Synonyms for this gene include CC-CKR-3, CD193 and CKR3. The Genbank reference sequence for CCR3 is AF247361.1. All variants and isoforms are within the scope of the invention.

CCL11 also known as eosinophil chemotactic protein and eotaxin-1 is the ligand of CCR2 and CCR3 receptors. It is encoded by the CCL11 gene. This gene is encoded on three exons and is located on chromosome 17. Chemokine receptors for which CCL11 is a ligand include. The HGNC ID for this gene is 10610. The GenBank reference sequence for CCL11 is AB063614.1.

Antagonists or inhibitors according to the present invention are intended to be therapeutic agents that inhibit directly or indirectly the biological activity of CCR2/CCL2, CCR2/CCL7, CCR2/CCL13, CXCR4/CXCL12 and/or CCR3/CCL11 receptor/ligand pairs. Such agents may include small molecules (organic or inorganic), natural products, synthetic compounds, antibodies (e.g., polyclonal sera, monoclonal, chimeric, humanized, human), antibody fragments such as recombinant antibody fragments, single-chain antibodies (scFv), single antibody variable domains, single antibody domain proteins (dAbs), antigen binding fragments, nucleic acid agents such as antisenses, ribozymes, DNAzymes, or RNA interference RNAi, siRNA, or shRNAs, which act by reducing chemokine receptors expression, proteins, peptides, peptide derivatives, peptidomimetics, carbohydrates or any other compound or composition which preferably decreases the activity of the chemokine receptor CXCR4 either by effectively reducing the amount of CXCR4 present on a cell, or by inhibiting the interactions of the ligand CXCL12, particularly of CXCL12-α. Antagonist compounds may also include variants, isoforms, solvates, hydrates, pharmaceutically acceptable salts, tautomers, stereoisomers, and prodrugs of the antagonist compounds.

According to a preferred embodiment, compositions and methods of use of the present invention preferably comprise antagonists of chemokine receptor CXCR4 inhibit one or more biological functions or bioactivity associated with CXCR4, by inhibiting the binding of one or more ligands (e.g., CXCL12-α and/or CXCL12-β (SDF-1-α or SDF-1-β)) to CXCR4 and/or inhibit signal transduction mediated through CXCR4. Accordingly, CXCR4-mediated processes and cellular responses (e.g., proliferation, migration, chemotactic responses and differentiation of fibrocytes) can be inhibited by CXCR4 antagonists.

CXCR4 antagonists have been extensively searched in the past since CXCR4 has been initially discovered as one of the co-receptors involved in human immunodeficiency virus cell entry. Numerous compounds have thus been chemically well characterized, and identified as significantly inhibiting CXCR4 and the axis CXCR4/CXCL12. The first CXCR4 antagonists which have been developed were peptide derivatives. Subsequent CXCR4 antagonists were cationic molecules able to bind the predominantly anionic extracellular domain of CXCR4. To date more than 20 different chemical classes have been described as CXCR4 antagonists. Numerous articles have been published describing molecules having CXCR4 antagonistic activity based on their chemical scaffolds (Debnath B et al., Theranostics. 2013; 3(1): 47-75).

Small molecules are the first class of compounds which may be used in the compositions CXCR4 antagonists according to the present invention. These are well-known in the art and have been described in details as CXCR4 antagonists inter alia in Wilson L J et al. Drug Development Research. 2011; 72:598-602). They include cyclam mimetics, bis-macrocycles, such as in particular bis-tetraazamacrocycles (Bicyclams) and derivatives thereof, quinolone-based CXCR4 antagonists, tetrahydroquinoline-based CXCR4 antagonists, guanidine-based CXCR4 antagonists, N-substituted indole-based CXCR4 antagonists, and/or pyrimidine-based CXCR4 antagonists, 1,4-phenylenebis (methylene) derivatives, and N-containing heterocycles.

Bicyclams have been described inter alia in the international publication No. WO00/56729. Among bicyclam molecules, we can cite para-xylyl-enediamine-based compounds like Plerixafor also designated as AMD3100 and which is commercialized by Genzyme Corporation under the tradename Mozobil and described inter alia in U.S. Pat. No. 5,583,131; and by Uy et al., Expert Opin Biol Ther. 2008 November; 8(11):1797-804. doi: 10.1517/14712598.8.11.1797. Derivatives of Plerixafor or structurally modified compounds may also be used as antagonists in the composition of the present invention. Such derivatives may be aromatic linked polyamine macrocyclic compounds such as tetrafluoro derivatives of Plerixafor which are described inter alia in the international publication No. WO93/12096 and U.S. Pat. No. 5,583,131.

Analogues of Plerixafor, such as AMD3465 which has a single azamacrocyclic ring and subsequent nonmacrocyclic, orally active CXCR4 antagonists preserving a p-xylyl-enediamine linker between the two heterocyclic units of the compounds have been described by Bodart et al. (Biochem Pharmacol. 2009 Oct. 15; 78(8):993-1000). Another bis-azamacrocyclic, also designated AMD3329, has been identified by Bridger et al. (J. Med. Chem. 1999 Sep. 23; 42(19):3971-81), and is marketed by the company AnorMed.

Further derivatives of Plerixafor which may be used in the compositions and methods of the present invention have been designed starting from the bicyclam plerixafor and a peptidic CXCR4 antagonist (TN14003). These derivatives may be selected among N,N'-Di-2-pyridinyl-1,4-benzenedimethanamine, 4F-benzoyl-TN14003, also designated BKT-140 (Peled et al, Clin. Cancer Res. 2014 Jan. 15; 20(2):469-79); N,N'-(1,4-phenylenebis(methylene))dipyrimidin-2-amine, also designated MSX-122 (Liang et al, PLoS One. 2012; 7(4):e34038) which is in clinical phase for Refractory Metastatic or Locally Advanced Solid Tumors with the company Metastatix Inc as sponsor; and $N^1,N^4$-Di-2-pyridinyl-1,4-benzenedimethanamine, also designated as WZ811 (than W et al., J Med Chem. 2007 Nov. 15; 50(23):5655-64) and marketed by the companies Tocris Bioscience and Selleckchem (selleckchem.com/products/wz-811.html).

Further bicyclam mimetics include for example JM1657 described by De Clercq E et al., (Mini Rev Med Chem. 2005 September; 5(9):805-24) and have been described inter alia in the US publication No. 20060264451.

By way of examples of quinoline-based CXCR4 antagonists, we can cite chloroquines and hydroxychloroquines drugs, such as NSC56612 which is described inter alia by Kim J M L et al., PLoS One. 2012; 7(2):e31004).

Among tetrahydroquinoline-based CXCR4 antagonists, we can cite AMD070, a potent orally active CXCR4 antagonist. The unique structural feature of these compounds is the presence of a core structure, a substituted (R), (S) or (RS) (N'-(1H-benzimidazol-2-ylmethyl)-N'-5,6,7,8-tetrahydroquinolin-8-yl-1,4-alkylamine) that replaces the macrocyclic nucleus of bicyclams. It is marketed by the company AnorMed under the name AMD11070 and is under clinical investigation for the prevention of T-tropic HIV infection by NIAID (Crawford J B et al. Org. Process Res. Dev., 2008, 12 (5), pp 823-830).

Guanidine-based CXCR4 antagonists have been described inter alia by Wilkinson R A et al. (Antimicrob Agents Chemother. 2011; 55:255-63) as being small molecules containing multiple guanide or biguanide groups. We can cite for example NB325, e.g., a polyethylene-hexamethylene biguanide which has been described by Thakkar N et al. (Antimicrob Agents Chemother. 2009; 53:631-8;) and by Krebs F C et al. (Biomed Pharmacother. 2005; 59:438-45). Derivatives thereof were also described as including some features of the polyethylene-hexamethylene biguanide NB325, as well as the peptide T140 that has five guanide groups on the side chains of arginine residues. Other active derivatives include for example phenylguanides.

Indole-based CXCR4 antagonists have been also described by Ueda S, et al. (Bioorg Med Chem Lett. 2008; 18:4124-9) and include for example 5-aminoindole-2-carboxylic acid.

Pyrimidine-based antagonists have been described inter alia in patent publications Nos. WO2010/147094 and US 2009/0143302.

TG-0054 has been described by Hsu et al (Cell Transplant. 2014 May 12) as an injectable small molecule and a potent selective CXCR4 antagonist. It also known under the tradename Burixafor from TaiGen Biopharmaceuticals Holdings Ltd., and has been tested for multiple myeloma, non-Hodgkin lymphoma, and Hodgkin disease and (ClinicalTrials.gov Identifier: NCT01018979).

Other compounds include an orally active low molecular weight non-peptide compound KRH-3955 which has been described inter alia by Nakasone T et al., (Med Microbiol Immunol. 2013 April; 202(2):175-82); a ghrelin receptor blocker (D-[Lys3] GHRP-6) which has been described by Patel K et al. (Int J Biol Sci. 2012; 8:108-17); diketopiperazine mimetics, thiazolylisothiourea derivatives, benzodiazepines, and dipicolylamine-zinc(II) complexes.

Compositions and methods of use according to the present invention may also comprise peptide-based CXCR4 antagonists. Some of these peptides have been described inter alia by Costantini S et al. (J Pept Sci. 2014 April; 20(4):270-8).

By way of examples, we can cite cyclic pentapeptidic-based CXCR4 antagonists, such as T22 ([Tyr5,12, Lys7]-polyphemusin II), T140 and T134 which are a highly potent CXCR4 antagonists, described by Tamamura H et al. (BBRC, 1998 Dec. 30; 253(3):877-82; Bioorg Med Chem Lett. 2001 Feb. 12; 11(3):359-62; FEBS Lett. 2004 Jul. 2; 569(1-3):99-104). In particular, it has been described that four amino acid residues indispensable for activity of peptide T140: Arg2, L-3-(2-naphthyl) alanine3 (Nal3), Tyr5 and Arg14. These key residues have been found to be positioned across the disulfide bridge and close in the T140 three-dimensional structure. Tamamura H et al. (FEBS Lett. Volume 550, Issues 1-3, 28 Aug. 2003, Pages 79-83) also described T140 analogs, such as TC14012, TE14005, and TN14003, as CXCR4 antagonists.

Another cyclopentapeptide CXCR4 antagonist which may be used in the compositions and methods of the present invention is FC131. This cyclopentapeptide has the following formula: Cyclo[2-Nal-Gly-D-Tyr-Arg-Arg] (SEQ ID NO: 10) wherein Nal is 2-naphthylalanine, Arg is arginine, Tyr is tyrosine, and Gly is glycine. It has been described inter alia by Yoshikawa Y et al. (Bioorg Med Chem Lett. 2012 Mar. 15; 22(6):2146-50) is a potent and orally active peptidomimetic CXCR4 inhibitor, and is marketed by the company Tocris Bioscience. FC122 has been also described as an analogue of FC131 wherein an arginine residue has been replaced by the epimeric N-methyl-D-arginine. Further (E)-alkene and (Z)-fluoroalkene analogs of F131 and FC122 have been described as CXCR4 antagonists (Narumi T, et al., Org Biomol Chem. 2010; 8:616-21).

Further CXCR4 antagonists having cyclic tetrapeptidic scaffolds have been described by Tamamura H et al. (J Med Chem. 2005; 48:3280-9).

Other modified peptides which may be used as CXCR4 antagonists include for examples CTCE-9908, a 17 amino acid peptide, which is a dimer of the 8 amino acid N-terminal sequence with modified P to G, bridges by lysine, described by Wong et al (BMC Urology, January 2014, 14:12) and marketed by the company Chemokine Therapeutics Corp; POL6326 described as being a recombinant protein designed via protein epitope mimetic by De Nigris F et al. (Recent Pat Anticancer Drug Discov. 2012 September; 7(3):251-64) and marketed by Polyphor Ltd; LY2510924 which has been described by Peng S B et al. (Mol Cancer Ther. 2015 February; 14(2):480-90); GST-NT21MP described by Galsky M D et al. (Clin Cancer Res. 2014 Jul. 1; 20(13):3581-8).

According to the present invention, CXCR4 inhibitor may further be an antibody-based moiety directed against the CXCR4 receptor, which antibody-based moiety is capable of acting as a CXCL12 antagonist. Human monoclonal antibodies have been extensively described inter alia by Carnec X et al., J Virol. 2005 February; 79(3): 1930-1933, and in US publication No. 2014/0322208. One of the fully human monoclonal antibodies, BMS-936564, (designated F7 in the international publication No. WO 2008/060367) and also previously designated MDX-1338. Numerous other monoclonal antibodies directed against the N-terminal part, extracellular loops ECL1, ECL2, or ECL3 of CXCR4. For example anti-CXCR4 monoclonal antibody A145 has been described as directed against the N-terminus, whereas the monoclonal antibody A120 is directed against a conformational epitope consisting of extracellular loops ECL1 and ECL2, and the monoclonal antibody A80 mAb is directed against ECL3 of CXCR4 (Adachi T et al., Retrovirology. 2011 Oct. 22; 8:84). Other human anti-CXCR4 antibodies have been widely marketed for example by the companies Thermofisher Scientific, R&D Systems, etc. . . . and include anti-CXCR4 monoclonal antibody 12G5, monoclonal antibody 708, monoclonal antibody 716 and monoclonal antibody 717 (marketed by the company R&D Systems under catalog Nos. MAB170, MAB171, MAB172 and MAB173), monoclonal antibody 2B11, 44717.111, 44716.111, 44708.111 (R&D Systems, Minneapolis, Minn., also see Stalmeijer et al, J Virol. March 2004; 78(6): 2722-2728).

Also included within the scope of invention are antagonists to CXCR4 ligand, e.g., CXCL12-α and/or CXCL12-β (SDF-1-α or SDF-1-β)) antagonists, which can include small organic or synthetic molecules, natural products, peptides, proteins, peptidomimetics, antibodies, antigen binding fragments, nucleic acid agents and the like. SDF-1 truncations, variants, mutant proteins or "muteins" having the ability to bind CXCR4 and have antagonistic activity may also be used to practice the method of the invention.

Nucleic acid inhibitors of SDF-1 activity have also been described and may be used in the compositions of the present invention. These nucleic acid-based inhibitors may function at either the receptor binding level or the gene expression and translational levels. The nucleic acid inhibitors of CXCR4 activity include, without limitations, nucleic acid enzymes (such as ribozymes), nucleic acid aptamers, antisense nucleic acids, and RNAi, such as siRNA. Nucleic acid CXCR4 inhibitors have been described in the following references: U.S. Pat. No. 6,429,308B1; US Publication No. 2005/0124569A1; U.S. Pat. No. 6,916,653B2; and US Publication No. 2005/0202077. Such nucleic acid inhibitors can include an antisense oligonucleotide which is complementary to some parts of base sequences of chromosomal DNA and/or RNA encoding CXCR4 protein. The antisense oligonucleotide of the present invention may be DNA or RNA.

Specifically antisense oligonucleotide can be complimentary to the base sequence containing initiation codon region from +61 to +91 when the gene transcription initiation point of mRNA encoding CXCR4 protein is to be +1, and at the same time hybridizes stably with the said sequence specifically and blocks the translation into a protein so as to have a function to inhibit the biosynthesis of the CXCR4 protein. Alternatively it could be siNA that can be unmodified or chemically-modified whereby the use of chemically-modified siNA improves various properties of native siNA molecules through increased resistance to nuclease degradation in vivo and/or through improved cellular uptake as elaborated in US Publication No. 2005/0202077. Also included within scope are mRNA coding for the CXCR4 proteins that can be cleaved by hammerhead ribozymes so as to effectively block production of these proteins as described in U.S. Pat. No. 6,916,653B2. Further within scope are siNAs that may be effectively employed in coOmpositions to include the siRNA sequences corresponding to the target sequences provided in SEQ ID NO: 101-823 of US Publication No. 2005/0202077.

According to another embodiment, compositions and methods of use of the present invention, antagonists of chemokine receptor CCR2 prevent the biological functions or bioactivity associated with CCR2, its isoforms or variants including CCR2A or CCR2B, in fibrocytes that display the receptor or antagonists which bind MCP-1/CCL2 or CCR2 or which prevent the binding of CCR2 with its cognate ligand(s) and thereby inhibit CCR2 biological functions. In particular, antagonists of CCR2 may inhibit the binding of one or more ligands (e.g., MCP-1, MCP-2, MCP-3, MCP-4, MCP-5, CCL2, CCL8, CCL16 and the like) to CCR2 and/or inhibit signal transduction mediated through CCR2 (e.g., GDP/GTP exchange by CCR2 associated G proteins, intracellular calcium flux), thereby inhibiting CCR2-mediated processes and cellular responses and functions.

Molecules that can antagonize one or more functions of CCR2 are well known in the art. In particular, several potent, orally bioavailable small molecule CCR2 receptor antagonists have entered the drug development phase for various indications.

By way of examples, we can cite a small molecule marketed by the company AstraZeneca designated AZD2423 and described inter alia by Kalliomaki et al., (Pain 2013 May; 154(5):761-7); a small molecule developed by the company UCB Research under the designation UCB102405 and has been described inter alia by Higgins P J et al. (Progress in inflammation research, Vol. 2, 2007, pages 115-123); an antagonist developed by Johnson & Johnson Pharmaceutical Research & Development, L.L.C. under the designation JNJ-17166864 (ClinicalTrials.gov Identifier: NCT00604123 and also described in the publication Anti-Inflammatory Drug Discovery edited by Jeremy I. Levin, Stefan Laufer, Page 378); RS 504393 (Mirzadegan et al, Aug. 18, 2000 The Journal of Biological Chemistry, 275, 25562-25571), RS 102895 hydrochloride (Seok et al, Nephrol. Dial. Transplant. 2013 July; 28(7):1700-10); CCR2 antagonists based on piperazine derivatives developed by the company Teijin and described inter alia in the international publication No. WO 97/44329.

Incyte Corporation also developed numerous small molecules CCR2 antagonists under the designation INCB-8696 (Matera et al., Expert Opin. Emerging Drugs (2012) 17(1): 61-82); pyridinylcyclohexyl-3-pyrrolidinyl derivative INCB-3284 (Xue C B et al., ACS Med. Chem. Lett., 2011, 2(6), pp450-454); Benzodioxolhydroxycyclohexyl derivative INCB3344 (Brodmerkel C M et al., J. Immunol. 2005 Oct. 15; 175(8):5370-8.), several (S)-3-aminopyrrolidine series of CCR2 antagonists under the designation PF-4136309 or INCB8761 (Xue C B et al., ACS Med Chem Lett. 2011 Oct. 5; 2(12):913-8); INCB3284 dimesylate (Mcmillin et al., J Neuroinflammation. 2014 Jul. 10; 11:121).

We can also cite the small molecule CCX140-B developed by ChemoCentryx (De Zeeuw D et al., Lancet Diabetes Endocrinol. 2015 September; 3(9):687-96); D-erythro-Pentitol derivative MK-0812 developed by the company Haihang Industry Co., Ltd. (Wisniewski T et al., J Immunol Methods. 2010 Jan. 31; 352(1-2):101-10).

The company Pfizer developed a CCR2 receptor antagonist under the designation PF-04634817 (ClinicalTrials.gov Identifier: NCT01994291), as well as hexanoic amide derivative based CCR2 inhibitors which have been described inter alia in the international publication No. WO 98/38167.

The company Bristol-Myers Squibb has developed a lactam-based compound BMS-741672 (ClinicalTrials.gov Identifier: NCT00699790), and another antagonist designated BMS-813160 or (S)-1-[(1S,2R,4R)-4-isopropyl (methyl)amino)-2-propylcyclohexyl]-3-(6-(trifluoromethyl) quinazolin-4-ylamino)pyrrolidin-2-one (ClinicalTrials.gov Identifier: NCT01752985); BMS CCR2 22 (Kredel et al., J Biomol. Screen. 2011 August; 16(7):683-93), Several tetrahydropyranyl cyclopentyl tetrahydropyridopyridine compounds have been described as CCR2 antagonists and developed by the company Merck, and in particular the (1R,3S)-3-Isopropyl-3-{[3-(trifluoromethyl)-7,8-dihydro-1,6-naphthyridin-6(5H)-yl]carbonyl}cyclopentyl) [(3S,4S)-3-methoxytetrahydro-2H-pyran-4-yl]amine which has been described inter alia in the international publication No. WO2005044264. Merck also develop 3-arylpiperidine based CCR2 antagonists as described in the international publication No. WO 98/31364.

Several other small molecules have been described and include 3 [(3S,4R)-1-((1R,3S)-3-isopropyl-2-oxo-3-{[6-(trifluoromethyl)-2H-1,3-benz-oxazin-3 (4H)-yllmethyl}cyclopentyl)-3-methylpiperidin-4-yl]benzoic acid; (3S,48)-N-((1R,3S)-3-isopropyl-3-{[7-(trifluoromethyl)-3,4-dihydroisoquinolin-2(1B)-yl]carbonyl}cyclopentyl)-3-methyltetrahydro-2H-p-yran-4-aminium; 3-[(3 S,4R or 3R,4S)-1-((1R,3S)-3-Isopropyl-3-{[6-(trifluoromethyl)-2H-1,3-benzoxazin-3-(4H)-yl]carbonyl}cyclopentyl)-3-methyl piperidin-4-yl]benzoic acid, and are by Brodmerkel et al., (J. Immunol, 2005, 175:5370-7378) and in the international publication No. WO2012138880.

Numerous other derivatives have been described as CCR2 antagonists. By way of examples, we can cite piperidinyl derivatives (WO2012075115), diazepam derivatives (WO2011048032), cyclohexane derivatives (WO2010121046), carboxamide derivatives (WO2010070032), cyclopentyl/cyclohexyl derivatives (WO2013152269), bicyclic heterocycles (WO2011042399), indole derivatives (WO2012125662), mercapto derivatives (WO2005118578), dipiperidine derivatives (WO2006036527), heteroaryl sulfonamides (US20100056509), fused heteroaryl pyridyl and phenyl benzenesuflonamides (WO2009009740).

Several CCR2 antagonist peptides have been also developed and have been described inter alia in the international publication NO. WO 2013000922. By way of examples we can cite the heptapeptide LGTFLKC called "ECL1 (C) inverso", "ECL1 (C)" having an amino acid sequence CKLFTGL, "ECL2 (N)" having an amino acid sequence LFTKC (SEQ ID NO: 2), "ECL2 (N) inverso" having an amino acid sequence CKTFL(SEQ ID NO: 3), "ECL3 (C)" having an amino acid sequence HTLMRNL (SEQ ID NO: 4) "ECL3 (C) inverso" having an amino acid sequence LNRMLTH (SEQ ID NO: 5), "ECL3 (N)" having an amino acid sequence LNTFQEF (SEQ ID NO: 6), "ECL3 inverso" having an amino acid sequence FEQFTNL (SEQ ID NO: 7), and/or peptides comprising the sequence Thr-Phe-Leu-Lys (SEQ ID NO: 8).

Alternatively, CCR2 antagonists may be anti-CCR2 antibodies and antibody fragments. A number of anti-CCR2 antibodies are known in the art and are available commercially. The company Biolegend has developed several anti-human CD192 CCR2) antibodies (see biolegend.com/cd192-ccr2-antibodies-6166/). We can also cite in particular monoclonal anti-CCR2 antibody 1D9 (ATCC HB-12549), 8G2 (ATCC HB-12550), LS132 which has described in international publication No. WO 01/57226, human CCR2 blocking antibody such as MLN1202 (Millennium Pharmaceuticals, Cambridge, Mass.), or a human antibody that neutralizes human CCL2, e.g., carlumab (CNTO 888; Centocor, Inc.) which has been described by Loberg et al., Cancer. Res. 67(19):9417 (2007).

Also included within the scope of invention are antagonists to CCR2 ligand, for example of MCP-1 (CCL2), CCL7, and/or CCL13.

Such antagonists may be anti-MCP-1 antibodies which are well known and well described in the literature. As anti-MCP-1 antibodies, we can cite antibodies capable of binding a plurality of beta-chemokines including MCP-1 were disclosed (WO03048083) and an MCP-I binding antibody which also binds eotaxin (US20040047860). Antibodies which selectively bind and neutralize mouse homologs of human MCP-1/CCL2 or human MCP-1/CCL2 like antihuman MCP-1/CCL2 antibody designated C775 which has been described in US 20090297502, as well as human anti MCP-1/CCL2 antibody designated CNT0888 (WO2006125202).

The compositions of the present invention may also comprise MCP-1/CCL2 truncations, variants, mutant proteins or "muteins" which have the ability to bind CCR2 and have antagonistic activity. Variants of homodimer forming chemokines, such as CCL2, having a single amino acid substitution in the dimerization interface that alters the pattern of hydrogen bonds, so as to result in an obligate monomer that binds to the receptor and has agonistic properties in vitro but which can antagonize natural chemokines and have anti-inflammatory activity in vivo as taught in international publication WO05037305A1 are among the variants useful in practicing the present invention. A peptide antagonist of MCP-1, is the truncated MCP-1 (9-76) (Jiang-Hong Gong, et al, J. Exp. Med. 1997, 186: 131).

Antagonists of ligand CCL7 and CCL13 include small organic or synthetic molecules, natural products, peptides, proteins, peptidomimetics, antibodies, antigen binding fragments, nucleic acid agents and the like. Peptide antagonists of CCL7 and/or of CCL13 may typically be fragments of CCL7 and/or CCL13 that compete with full-length CCL7 and/or with full length of CCL13 for binding to CCR2 and hence antagonise CCL7 and/or CCL13. Using known techniques and based on knowledge of the sequence of CCL7, double-stranded RNA (dsRNA) or single-stranded antisense RNA molecules can be designed to antagonise the target by sequence homology-based targeting of its RNA. Such dsRNAs or ssRNA will typically be small interfering RNAs (siRNAs), usually in a stem-loop ("hairpin") configuration, or micro-RNAs (miRNAs). The sequence of such dsRNAs or ssRNA will comprise a portion that corresponds with that of a portion of the mRNA encoding the target. This portion will usually be 100% complementary to the target portion within the target mRNA but lower levels of complementarity (e.g. 90% or more or 95% or more) may also be used.

As antagonists of CCL7, we may cite anti-CCL7 antibodies having CCL7 antagonist (blocking) properties. Preferred antagonists are monoclonal antibodies which specifically recognise an epitope within CCL7 and blocks the activity of CCL7, in particular the interaction between CCR2 and CCL7. Specifically monoclonal antibodies to CCL7 may include CCL7 monoclonal antibody marketed by the company Pierce antibodies under the designation CCL7 antibody h.mcp.3; Recombinant Human CCL7/MCPS protein marketed by the company Sino Biological Inc. (Catalog #11926-H08E); and the CCL7 antibody as marketed by the company Labome under the designation MA1-21385.

As antagonists of ligand CCL13, we may cite anti-CCL13 antibodies, such as antibodies from Novus, Origene, Labome, Sigma Aldrich etc. . . . . . Monoclonal antibodies against CCL13 include H00006357-M03 (Abnova), MCP-4/CCL13 Antibody 8C12 (Pierce Antibodies), MCP-4/CCL13 Antibody 3G4 (Pierce Antibodies), human CCL13/MCP-4 Antibody (R&D systems) etc. . . .

According to a further embodiment, compositions and methods of use of the present invention comprise antagonists of chemokine receptor CCR3 prevent one or more biological functions or bioactivity associated with CCR3. Such antagonist of CCR3 function can inhibit the binding of one or more ligands (e.g., CCL11, CCL26, CCL7, CCL13, CCL15, CCL24, CCL5, CCL28, CCL18) to CCR3 and/or inhibit signal transduction mediated through CCR3. Accordingly, CCR3-mediated processes and cellular responses and functions can be inhibited by antagonists of CCR3. As used herein, "CCR3" refers to naturally occurring CC chemokine receptor 3 (e.g. mammalian CCR3 (e.g., human {*Homo sapiens*) CCR3) and encompasses naturally occurring variants, such as allelic variants and splice variants.

Numerous molecules have been described in the art as antagonists of one or more functions of CCR3 receptor. Compositions and methods of use according to the present invention may comprise small molecule based CCR3 antagonists. By way of examples, we can cite small molecules CCR3 antagonists such as the oral candidate GW776994 which has been developed by GSK (Neighbour H et al., Clin Exp Allergy. 2014 April; 44(4):508-16), benzylpiperidine substituted aryl urea derivative DPC-168 (Pruitt J R et al., Bioorganic & Medicinal Chemistry Letters July 2007), the compound (S)-methyl-2-naphthoylamino-3-(4-nitrophenyl) propionate which is marketed by the company Calbiochem under the name SB328437 and described inter alia by Mori A et al., (Int Immunol. 2007 August; 19(8):913-21), as well as the N-Benzoyl-4-nitroaniline ethyl ester SB297006 also described by Mori A. et al., (Int Immunol. 2007 August; 19(8):913-21), the small molecules developed by AstraZeneca such as AZD1744 (Neighbour H. et al., Current Opinion in Drug Discovery & Development 2010 13(4):414-427) and AZD 3778 (Greiff L. et al., Respir Res. 2010 Feb. 9; 11:17), the trans-1,2-disubstituted cyclohexane derivative developed by Bristol-Myer Squib under the designation BMS639623 and described by Santella J B et al., (Bioorg Med Chem Lett. 2008 Jan. 15; 18(2):576-85), the oral antagonist YM-344031 which is described inter alia by Suzuki K et al., (BBRC 2006 Jan. 27; 339(4):1217-23); A-122058 as described by Neighbour H et al., (Current Opinion in Drug Discovery & Development 2010 13(4): 414-427); (S)—N-((1R,3S,5S)-8-((6-fluoronaphthalen-2-yl) methyl)-8-azabicyclo[3.2.1]octan-3-yl)-N-(2-nitrophenyl) pyrrolidine-1,2-dicarboxamide, (R)-1-(1-((6-fluoronaphthalen-2-yl)methyl) pyrrolidin-3-yl)-3-(2-(2-hydroxyethoxy) phenyl)urea; morpholin-acetamide-based compound such as the 4-[[(2s)-4-[(3,4-dichlorophenyl)methyl]-2-morpholinyl-methyl-aminocarbonyl]-aminomethylbenzamide; and morpholine urea based compound N-[[(2S)-4-[(3,4-difluoro phenyl)methyl]-2-morpholinyl]-methyl]-3-[(methylsulfonyl)amino]-benzeneacetamide.

Other well-known CCR3 antagonists include 2-mercaptobenzothiazole derivatives, aryl or phenyl sulfonamide derivatives (WO2012051090), bridged bicyclic amine derivatives (WO2004076448), diazepam derivatives (WO2011048032), substituted piperidines (WO2010115836), pyrollidinyl alkylamide derivatives (WO2011042399), bicyclic heterocycles (WO2011013078) piperidyl derivatives (WO2008049874), amino alkyl amide derivatives (WO2007034251), imidazole derivatives (WO2007025751), azetidine derivatives (WO03077907), pyran derivatives (WO2010069979), substituted pyrimidine derivatives (WO2004004731), or morpholinyl derivatives (WO03099798).

Antibody-based CCR3 antagonists have also been developed and include for example of PE anti-human CD193 (CCR3) antibody available from the company Biolegend, anti-CCR3 antibodies ab32512, ab36827, ab36829, ab36827, ab1667, ab16231, ab157139 available from Abcam, Y31 from OriGene, eBio5E8-G9-B4 from eBioscience, human CCR3 MAb (Clone 61828) from R&D systems. See also U.S. Pat. Nos. 6,806,061 and 6,207,155, and in U.S. published applications Nos. 20050191702, 20050069955, and 20020147312 for exemplary antibodies which specifically bind and inhibit the CCR3 receptor and U.S. Pat. Nos. 6,946,546 and 6,635,251, as well as U.S. published applications 20040191255 and 20040014132 for exemplary antibodies.

Additional compounds for inhibiting the CCR3 receptor include RNA, DNA or RNA/DNA aptamers directed against CCR3. In particular aptamers have been described in U.S. Pat. Nos. 5,270,163, 5,840,867, 6,180,348 and 6,699,843. Other compounds for inhibiting the CCR3 receptor include anti-sense oligonucleotides or siRNAs directed against CCR3, eotaxin-1, eotaxin-2 or eotaxin-3, including the anti-sense oligonucleotides directed against the CCR3 receptor such as that described in U.S. Pat. No. 6,822,087.

Peptide-based CCR3 antagonists may be derived from phage libraries, such as for example peptide CPWYFWPC (SEQ ID NO: 9) as described in by Houimel M et al. (Eur. J. Immunol. 2001 December; 31(12):3535-45) or peptide analogues of CCR3 as described in the international publication No. WO1999043711.

Also included within the scope of invention are antagonists to CCR3 ligand, such as for example CCL11 antagonists, which can include small organic or synthetic molecules, natural products, peptides, proteins, peptidomimetics, antibodies, antigen binding fragments, nucleic acid agents and the like. CCL11 truncations, variants, mutant proteins or "muteins" having the ability to bind CCR3 and have antagonistic activity may also be used to practice the method of the invention. A particularly preferred CCR3 antagonist is naphthalenylcarbonyl derivative SB 328437.

The CCR2, CCR3 and/or CXCR4 antagonists suitable for use in accordance with the present invention can be administered alone but are generally administered in human therapy, in admixture with a suitable pharmaceutically acceptable vehicle, excipient, diluent, or carrier selected with regard to the intended route of administration and standard pharmaceutical practice. Such pharmaceutically acceptable vehicle or excipient may be present in an amount between 0.1% and less than 100% by weight. Optimizing drug-excipient ratios are with the reach of a person with ordinary skill in art for instance the desired weight ratio of drug/excipient in the composition could be less than or equal to the ratio of solubilities of drug/excipient, in a suitable medium.

Compositions according to the present invention are thus preferably pharmaceutical compositions for use in a method of treating and/or preventing COPD and AECOPDs and thus comprise a therapeutically effective amount of at least one antagonist or inhibitor of CCR2/CCL2, CCR2/CCL7, CCR2/CCL13, CXCR4/CXCL12 and/or CCR3/CCL11 receptor/ligand pairs and a pharmaceutically acceptable carrier. Such pharmaceutical compositions are efficient in reducing fibrocytes recruitment and migration associated with COPD and modulated via CCR2 and/or CCR3 and/or CXCR4.

A therapeutically effective amount is a predetermined amount sufficient to achieve an effective systemic concentration or local concentration in the tissue and desired effect, i.e., inhibiting or blocking/antagonizing one or more of the above receptor/ligand pairs. The specific dose of a compound administered according to this invention to obtain therapeutic and/or prophylactic effects will, of course, be determined by the physician depending on the conditions of the patients, weight, age and sex, compound administered, the route of administration, etc. . . .

Pharmaceutical compositions of the present invention may be administered orally, buccally, or sublingually, and may be in the form of tablets, capsules (including soft gel capsules), multiparticulate, gels, films, elixirs, solutions or suspensions, which may contain flavoring or coloring agents, for immediate-, delayed-, modified-, sustained-, dual-, controlled-release or pulsatile delivery applications. Such compounds may also be administered via fast dispersing or fast dissolving dosages forms or in the form of high energy dispersion or as coated particles. Suitable pharmaceutical formulations may be in coated or un-coated form as desired.

Such solid pharmaceutical compositions, for example, tablets may contain excipients such as microcrystalline cellulose, lactose, sodium citrate, calcium carbonate, dibasic calcium phosphate, glycine and starch, disintegrants such as sodium starch glycollate, croscarmellose sodium and certain complex silicates, and granulation binders such as polyvinylpyrrolidone, hydroxypropylmethyl cellulose (HPMC), hydroxypropylcellulose (HPC), hydroxypropyl methylcellulose acetate succinate (HPMCAS), sucrose, gelatin and acacia. Additionally, lubricating agents such as magnesium stearate, stearic acid, glyceryl behenate and talc may be included. Solid compositions of a similar type may also be employed as fillers in gelatin capsules or HPMC capsules. Excipients in this regard include lactose, starch, cellulose, milk sugar, or high molecular weight polyethylene glycols. For aqueous suspensions and/or elixirs, the CCR2, CCR3 and/or CXCR4 antagonists may be combined with various sweetening or flavoring agents, coloring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, HPMC, HPMCAS, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form, i.e., within the matrix, and/or on the dosage form, i.e., upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavoring, polyethylene glycol, fumed silica, silicon dioxide, sodium starch glycolate, sodi stearyl fumarate, sorbitol, xylitol. The terms dispersing or dissolving as used herein to describe FDDFs are dependent upon the solubility of the drug substance used, i.e., in cases where the drug substance is insolu fast dispersing dosage form can be prepared, and, in cases where the drug substance is soluble, a fast dissolving dosage form can be prepared.

Compositions and methods of use according to the present invention may be administered parenterally, for example, intracavemosally, intravenously, intra-arterially, intraperitoneally, intrathecally, intraventricularly, intraurethrally, intrasternally, intracranially, intramuscularly or subcutaneously, or they may be administered by infusion or needlefree techniques. For such parenteral administration they are best used in the form of a sterile aqueous solution, which may contain other substances, for example, enough salts or glucose to make the solution isotonic with blood. The aqueous solutions should be suitably buffered (preferably, to a pH of from about 3 to 9), if necessary. The preparation of suitable parenteral formulations under sterile conditions is readily accomplished by standard pharmaceutical techniques well known to those skilled in the art.

For oral and parenteral administration to patients may be daily dosage level of the CXCR4, CCR2 and/or CCR3 antagonists as determined by a physician and will vary with the age, weight and response of the particular patient. The dosage may be by a single dose, divided daily dose, or multiple daily doses. Alternatively, continuous dosing, such as for example, via a controlled (e.g., slow) release dosage form can be administered on a daily basis or for more than one day at a time.

Compositions according to the present invention may be administered intranasally or by inhalation and are conveniently delivered in the form of a dry powder inhaler or an aerosol spray presentation from a pressurized container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A(TM) or 1,1,1,2,3,3,3-heptafluoropropane (HFA 227EA(TM)), carbon dioxide or other suitable gas. In the case of a pressurized aerosol, the dosage unit may be determined by providing a valve to deliver a metered amount. The pressurized container, pump, spray or nebuliser may contain a solution or suspension of the active compound, e.g. using a mixture of ethanol and the propellant as the solvent, which may additionally contain a lubricant, e.g., sorbitan trioleate. Capsules and cartridges (gelatine capsule) for use in an inhaler or insufflator may be formulated to contain a powder mix of a compound of the invention and a suitable powder base such as lactose or starch.

Aerosol or dry powder formulations are preferably arranged so that each metered dose or "puff" contains a therapeutically effective amount of CXCR4, CCR2 and/or CCR3 antagonists for delivery to the patient to be treated. The overall daily dose with an aerosol will be in the range of from 1 to 50 mg, which may be administered, in a single dose or, more usually, in divided doses throughout the day. CXCR4, CCR2 and/or CCR3 antagonists suitable for use in accordance with the present invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, and oleic acid.

CXCR4, CCR2 and/or CCR3 antagonists suitable for use in accordance with the present invention may also be used in combination with a cyclodextrin. Cyclodextrins are known to form inclusion and non-inclusion complexes with drug molecules. Formation of a drug-cyclodextrin complex may modify the solubility, dissolution rate, and bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are some of the most commonly used and suitable examples are described in PCT Publication Nos. WO 91/11172, WO 94/02518 and WO 98/55148. According to the present invention, the oral administration is the preferred route.

In circumstances where the recipient suffers from a swallowing disorder or from impairment of drug absorption after oral administration, the drug may be administered parenterally, sublingually, or buccally. In the event that the agent is inactive orally then parenteral administration could be utilized.

Other possible formulations, such as nanoparticles, liposomes and immunologically based systems may also be used to administer an appropriate dose of the compositions antagonists according to the present invention.

Antagonists of CXCR4, CCR2 and/or CCR3 receptors may be administered singly or in any combination thereof. Further, CXCR4, CCR2 and/or CCR3 antagonists can be administered singly or in any combination thereof in a temporal sense, in that they may be administered simultaneously, before, and/or after each other. According to the disclosure provided herein, CXCR4, CCR2 and/or CCR3 antagonists are useful in reducing and/or inhibiting fibrocytes migration and differentiation and are thus useful for treating and/or preventing COPD as well as AECOPD.

The present invention also provides kits or pharmaceutical packages that include appropriate doses of the CXCR4 antagonists or compositions as described above for use in a method for the prevention and/or treatment of COPD and AECOPDs. In addition to compositions in the form of, for example, tablets, capsules, or lyophilized powders, the kits or pharmaceutical packages can include instructions for using and administering the composition for the prevention and/or treatment of COPD and AECOPDs. Such kits or packages may be provided in a bottle or another appropriate form (e.g., a blister pack). Optionally, the kits or pharmaceutical packages can also include other pharmaceutically active agents, and/or materials used in administration of the drug(s), such as diluents, needles, syringes, applicators, and the like.

In particular, pharmaceutical compositions and kits according to the present invention may be administered in association with other pharmaceutically active agents, such as for example bronchodilatators (LABA, LAMA), corticoids, and/or phosphodiesterase inhibitors either orally or by inhalation.

The present invention further provides a method of suppressing fibrocytes proliferation, migration and differentiation mediated and/or modulated by CXCR4, CCR2 and/or CCR3 in a subject having COPD or AECOPD or at a risk of developing COPD or AECOPD comprising administering to the subject a therapeutically effective amount of the pharmaceutical composition as described above.

According to a second embodiment, the present invention is directed to in vitro or in vivo method of screening or identifying agents that can be used in the methods of treatment and/or prevention described herein. The methods of screening according to the second embodiment may include determination of whether an agent inhibits CXCR4, CCR2 and/or CCR3 ligand binding and/or function followed by confirmation of it as being effective in treating and/or preventing COPD and/or AECOPDs. Alternatively, the screening methods can simply involve testing agents that are known to be CXCR4, CCR2 and/or CCR3 inhibitory therapeutic agents for their efficacy in treating and/or preventing COPD and/or AECOPDs. Testing an agent for its efficacy in altering CXCR4, CCR2 and/or CCR3 activities can be carried out using in vitro and/or in vivo methods that are well known in the art (Charo et al., (1994) PNAS 91, 2752-2756). Therapeutic efficacy of such active compounds can be determined by standard therapeutic procedures in cell cultures or in animal models, e.g., for determining the ED50 (the concentration of compound that produces 50% of the maximal effect). Such testing can be carried out in appropriate animal model systems for COPD and/or AECOPDs.

According to this embodiment, further antagonists of CXCR4, CCR2 and/or CCR3 functions may be identified, for example, by screening libraries of collections of molecules. Another source of antagonists of CXCR4, CCR2 and/or CCR3 functions may be combinatorial libraries, which can comprise many structurally distinct molecular species. Combinatorial libraries can be used to identify lead compounds or to optimize a previously identified lead. Such libraries can be manufactured by well-known methods of combinatorial chemistry and screened by suitable methods.

Other selective CXCR4, CCR2 and/or CCR3 antagonists can be identified using standard assays known to those skilled in the art. Briefly, one type of screen to identify selective modulators uses cell lines, including primary cells or CXCR4, CCR2 and/or CCR3 transfected cells. Alternatively, animal models could be utilized.

The method according to this embodiment of the present invention is thus particular useful for screening/identifying agents capable of decreasing fibrocytes migration and differentiation in COPD or during AECOPDs. Said method may comprise administering to a test animal over-expressing CXCR4, CCR2 and/or CCR3 and analyzing whether the amounts of CXCR4, CCR2 and/or CCR3 are decreased compared to the levels prior to administration of the test agent, wherein if the amounts of the CXCR4, CCR2 and/or CCR3 are decreased, the test agent is identified as an agent is capable of decreasing fibrocytes migration and differentiation in COPD and/or AECOPDs.

According to another embodiment, the present invention is directed to a method of assessing the risk of COPD or AECOPDs in a subject, comprising; a) obtaining a suitable sample from the said subject b) isolating and identifying the circulating fibrocytes in the said sample c) optionally assessing fibrocytes migration in the said sample and d) measuring the expression levels of CXCR4, CCR2 and/or CCR3 chemokine receptors, or preferably of CXCL12 chemokine, particularly of CXCL12-α in the said sample. Such method may further comprise a step of administering to the subject diagnosed with risk of developing COPD, AECOPD or diagnosed with COPD or AECOPD, an effective amount of the pharmaceutical composition as described above.

According to still another embodiment, the present invention provides an in vitro method of measuring the level of at least one gene selected from the group consisting of CXCR4, CCR2 and/or CCR3 in the peripheral blood fibrocytes. The present invention also provides a method for monitoring the response to a therapeutic agent in a patient suffering from COPD comprising the step of measuring the level of expression of at least one gene selected from the group consisting of CXCR4, CCR2 and/or CCR3 in the peripheral blood fibrocytes of the patient.

Throughout this application, various references are referred to and disclosures of these publications in their entireties are hereby incorporated by reference into this application to more fully describe the state of the art to which this invention pertains.

EXAMPLES

Example 1—Enrollment of Subject

Subjects aged more than 40 years were eligible for enrollment if they had a clinical diagnostic of COPD exacerbation according to the GOLD guidelines (Gold 1998. Global Initiative for Chronic Obstructive Lung Disease. Global Strategy for the Diagnosis, Management and Prevention for Chronic Obstructive Pulmonary Disease. NIH Publication—updated 2011). COPD patients with exacerbation have been recruited during hospitalization in Intensive care unit or as outpatients in the clinical investigation centre of the CHU de Bordeaux. 48 healthy volunteers without any history of lung disease and with normal lung function testing were recruited. Subjects are separated in 2 sub-groups according to smoking history (never smokers, former or current smokers) and paired to patients according to age and sex.

Main exclusion criteria for COPD patients and healthy subjects were asthma, lung fibrosis, idiopathic pulmonary hypertension and chronic viral infections (hepatitis, HIV). Exacerbating COPD patients and control subjects were enrolled in the "Firebrob" study. Additionally, COPD patients that have not exacerbated during a minimal period of one year were also recruited as outpatients in the clinical investigation centre of the CHU de Bordeaux ("Cobra" study). They are designed as "non-exacerbating COPD patients" in the following text. All subjects provided written informed consent. The study protocol was approved by the local research ethics committee and the French National Agency for Medicines and Health Products Safety.

Example 2—Design of the "Firebrob" Study

The study was conducted in centers group clinical trial during 3 years. A summary of the study is provided FIG. 1. The study has been registered under the N° NCT01196832 at ClinicalTrials.gov (i.e. "Firebrob" study).

There were two visits for exacerbating COPD patients: a visit during the exacerbation (inclusion, V1), a visit two months ±7 days after the exacerbation (stable state, V2). The inclusion visit (V1) consisted of the information and signature of the inform consent, taking blood sample (50 ml) for fibrocyte analysis. The second visit (V2) consisted of a clinical and functional evaluation (plethysmography, TLCO, arterial gaz) and taking blood sample for fibrocyte analysis. There was one visit for control subjects and "non-exacerbating COPD patients", during which the inform consent was signed, a clinical and functional evaluation was performed (plethysmography, TLCO, arterial gaz), and blood sample was taken for fibrocyte analysis.

Example 3—Design of the "Cobra" Study

There was one visit "non-exacerbating COPD patients", during which the inform consent was signed, a clinical and functional evaluation was performed (plethysmography, TLCO, arterial gaz), and blood sample was taken for fibrocyte analysis.

The study have been registered under the N° CPP 0811738 (i.e. "Cobra" study)

Example 4—Circulating Fibrocytes

Purification of nonadherent non-T (NANT) cells was performed. Briefly, peripheral blood mononuclear cells (PBMC) were separated from whole blood by Ficoll-Hypaque density gradient centrifugation. After the first centrifugation at 150 g for 15 min, the top plasma layer was harvested and kept at −80° C. for further analysis. Mononuclear cells at the interface were harvested, washed once with 1×PBS. Erythrocyte lysis was performed by adding 20 ml of hypotonic 0.2% NaCl solution during 30s, followed by adding 20 ml of 1.6% NaCl to end with an isotonic solution. Mononuclear cells were again washed with 1×PBS, resuspended in Dulbecco's modified Eagle medium (DMEM), 4.5 g/l glucose, L-glutamine, supplemented with 20% fetal bovine serum (FBS), penicillin/streptomycin and MEM non essential amino acid and incubated 1 h at 37° C. The non-adherent mononuclear cell fraction was taken and washed in cold 1×PBS 0.5% BSA, 2 mM EDTA. T-cells were further depleted with anti-CD3 monoclonal antibody (Miltenyi Biotech). At least $0.2 \times 10^6$ nonadherent non-T (NANT) cells were distributed in each FACS tube and fixed overnight with Cytofix/Cytoperm (eBioscience).

Example 5—Identification and Characterization of Circulating Fibrocytes

Fibrocytes were identified by flow cytometry as double positive for the surface marker CD45 and the intracellular marker collagen I. Fixed blood NANT cells were washed in permeabilization buffer (eBioscience) and incubated either with mouse anti-human collagen I antibodies (Millipore Cat # MAB3391, RRID:AB_94839) or with matched IgG1 isotype control (Santa Cruz Biotechnology Cat # sc-3877, RRID:AB_737222), followed by fluorescein isothiocyanate (FITC)-conjugated anti-mouse antibodies (Beckman Coulter Cat # IM0819). Next, the cell pellet was incubated either with allophycocyanin (APC)-conjugated anti-CD45 antibodies (BD Biosciences Cat #555485, RRID: AB_398600) or with matched APC-conjugated IgG1 isotype control (BD Biosciences Cat #555751, RRID:AB_398613). The cell suspension was analyzed with a BD FACSCanto II flow cytometer (BD Biosciences, San Jose, Calif.). Offline analysis was performed with FACSDiva software. The negative threshold for CD45 was set using a matched APC-conjugated IgG1 isotype control, and all subsequent samples were gated for the CD45 positive region. Cells gated for CD45 were analyzed for collagen-1 expression, with negative control thresholds set using FITC-stained cells. Specific staining for collagen-1 was determined as an increase in positive events over this threshold. Fibrocyte numbers were expressed as a percentage of total PBMC counts.

Example 6—Fibrocyte Migration

Fibrocyte migration was assessed using a modified Boyden chamber assay. The transwell inserts (pore size 8 µm) and the wells were coated for 1 h at room temperature with poly-lysine-ethylene glycol (PEG-PLL, Susos) to prevent cell adhesion. The inserts and the wells were rinsed with PBS. $0,3.10^6$ nonadherent non-T (NANT) cells resuspended in 0.2 ml resuspended in 0.2 ml DMEM, 4.5 g/l glucose, L-glutamine, supp DMEM, 4.5 g/l glucose, L-glutamine, supplemented with ITS, penicillin/streptomycin and MEM non essential amino acid were added to the upper compartment of each well. When indicated, NANT cells were pretreated for 1 h at 37° by 25 µg/ml plerixafor (Sigma-Aldrich) or 10 µM SB 328437 (R&D Systems) before being added to the upper compartment. Recombinant human CXCL12 (25 ng/ml to 200 ng/ml; R&D Systems), recombinant human CCL11 (25 ng/ml to 200 ng/ml; R&D Systems) or plasma (50% dilution) extracted from blood coming from COPD V1 patient or control subject was added to the bottom compartment of each well. After about 12 h, the content of bottom compartment was removed to assess fibrocyte migration by flow cytometry using double labeling CD45-collagen I. To obtain absolute values of migratory cells, flow cytometric counts for each condition were obtained during a constant predetermined time period (1 min). The fraction of migratory fibrocytes was defined by the ratio between the number CD45+coll I+ cells counted in the bottom chamber divided by the number of CD45+coll I+ cells added in the upper compartment. These values were normalized to the fraction of migratory fibrocytes obtained in the basal condition (medium only).

Example 7—Measurement of Plasma CXCL12 and CCL11

Plasma CXCL12 and CCL11 were measured by ELISA according the manufacturer's instructions (R&D Systems).

Example 8—Results of the Clinical Trial

Enrollment and Baseline Characteristics 58 exacerbating COPD patients and 48 control subjects were enrolled (FIG. 1). Level of fibrocytes in 48 exacerbating COPD patients (V1), in 9 non exacerbating COPD patients and in 38 control subjects were then quantified. Level of fibrocytes in 27 COPD patients at stable state (V2) was then quantified.

Circulating Blood Fibrocytes

Figure 2:
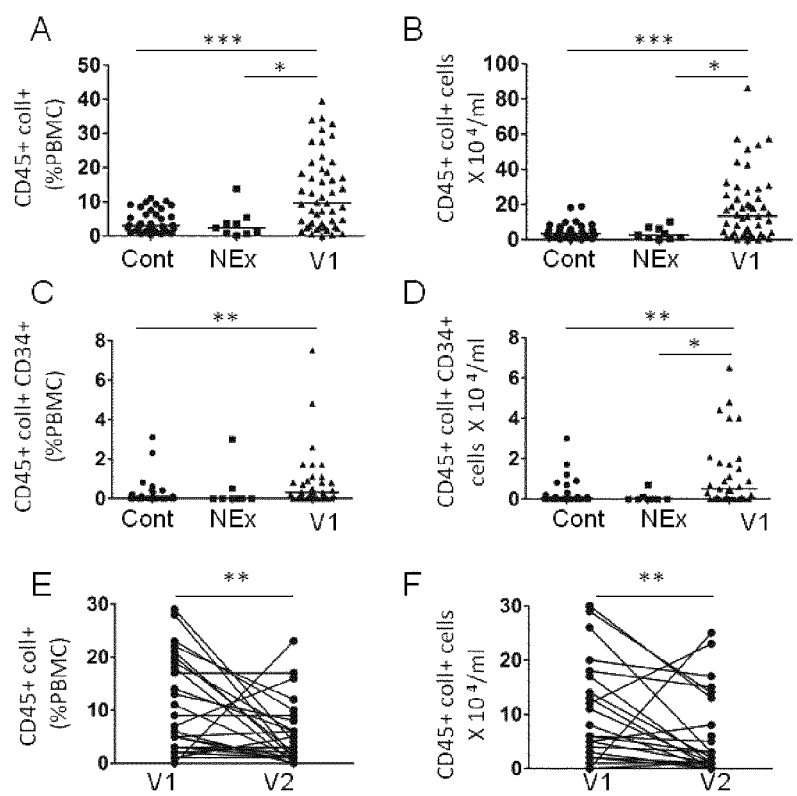
FIGS. 2A-F are graphs showing the percentage of CD45+ Coll+ cells in Peripheral Blood Mononuclear Cell (PBMC) (A) and concentration of fibrocytes in the blood (B) of control subjects ("Cont", n=38), non-exacerbating COPD patients ("NEx", n=9), exacerbating COPD patients ("V1", n=48) *: P<0.05, *** P<0.001, non-parametric Kruskal Wallis test. Percentage of CD45+ CD34+ Coll+ cells in PBMC (C) and concentration of fibrocytes in the blood (D) of control subjects ("Cont", n=25), non-exacerbating COPD patients ("NEx", n=8), exacerbating COPD patients ("V1", n=29) *: P<0.05, : P<0.01, non-parametric Kruskal Wallis test. Medians are represented as horizontal lines (A-D). Percentage of CD45+ Coll+ cells (E) and concentration of CD45+ Coll+ cells in the blood (F) in each exacerbating COPD patient at the time of exacerbation (V1) and 2 months after (V2)  P<0.01, Wilcoxon matched pairs test.

The percentage of blood fibrocytes (CD45+ Coll+ cells) was higher in patients with COPD during exacerbation ("V1", median=9.6 (95% confidence interval [CI], 9.5 to 15.7) of PBMC, n=48) compared with "non-exacerbating COPD patients" ("Nex", median=2.4 (95% CI, 0.3 to 6.8) of PBMC, n=9, p<0.05) and in control subjects (median=3.0 (95% CI, 3.1 to 5.3) of PBMC, n=38, p<0.001) (FIG. 2A). Similar results were obtained in the fibrocyte level when expressed as absolute counts per milliliter of blood (FIG. 2B). Both the percentage (FIG. 2C) and the absolute number (FIG. 2D) of circulating CD34-positive fibrocytes were increased in exacerbating COPD patients as compared to those in control subjects. However, when separating subgroups of exacerbating COPD patients, based on their treatment for the exacerbation of COPD (antibiotic, oral corticoids), ventilation mode (spontaneous ventilation, non-invasive ventilation or intubation), presence or absence of hospitalization, no significant differences in fibrocytes between the different subgroups were observed (data not shown).

Two months after exacerbation ("V2"), both the percentage (FIG. 2E) and the absolute number (FIG. 2F) of fibrocytes were significantly reduced as compared to those assessed at V1 (p<0.01). Moreover, there was a significant increase in the percentage of fibrocytes at V2 in a subgroup of patients with 2 or more unscheduled visit for COPD the year before V1 and that without any unscheduled visit (Figure E1).

Relationships Between Fibrocytes, Survival and Both Functional and Clinical Parameters Survival data were collected in COPD patients for a median period of 1.4 year and up to 3 years after V1. Kaplan-Meier survival analysis was performed in 2 subgroups of patients based on the percentage of fibrocytes assessed at V1. Patients with more than 28% fibrocytes had a significant reduced life expectancy compared with patients with less than 28% fibrocytes (FIG. 3A). There was no statistical difference between the 2 subgroups in terms of sex ratio, age, FEV1, FVC, PaO2 (data not shown). The subgroup of patients with more than 28% fibrocytes consisted of 6 patients with acute exacerbation all requiring hospitalization, whereas the subgroup of patients with less than 28% fibrocytes consisted of 36 patients with acute exacerbation (20 requiring hospitalization and 16 without hospitalization).

Correlations coefficients between the percentages of fibrocytes assessed at the second visit (i.e., V2 two months after the exacerbation at a stable state) and various functional parameters were also determined. The percentage of fibrocytes was negatively and significantly correlated to FEV1 (% predicted, FIG. 3B), FVC (% predicted, FIG. 3C), the FEV1/FVC ratio (%, FIG. 3D), TLCO (% predicted, FIG. 3E) and $PaO_2$ (mmHg, FIG. 3F). Similar negative correlations were obtained between the percentage of circulating fibrocytes at the second visit and FEV1 (L), FVC (L) or FEF25-75 (L/s and % predicted) (Figure E2). By contrast, there was no significant correlation between the percentages of circulating fibrocytes of exacerbating patients with age (data not shown).

Fibrocyte Expression of Chemokine Receptors

Figure 4:
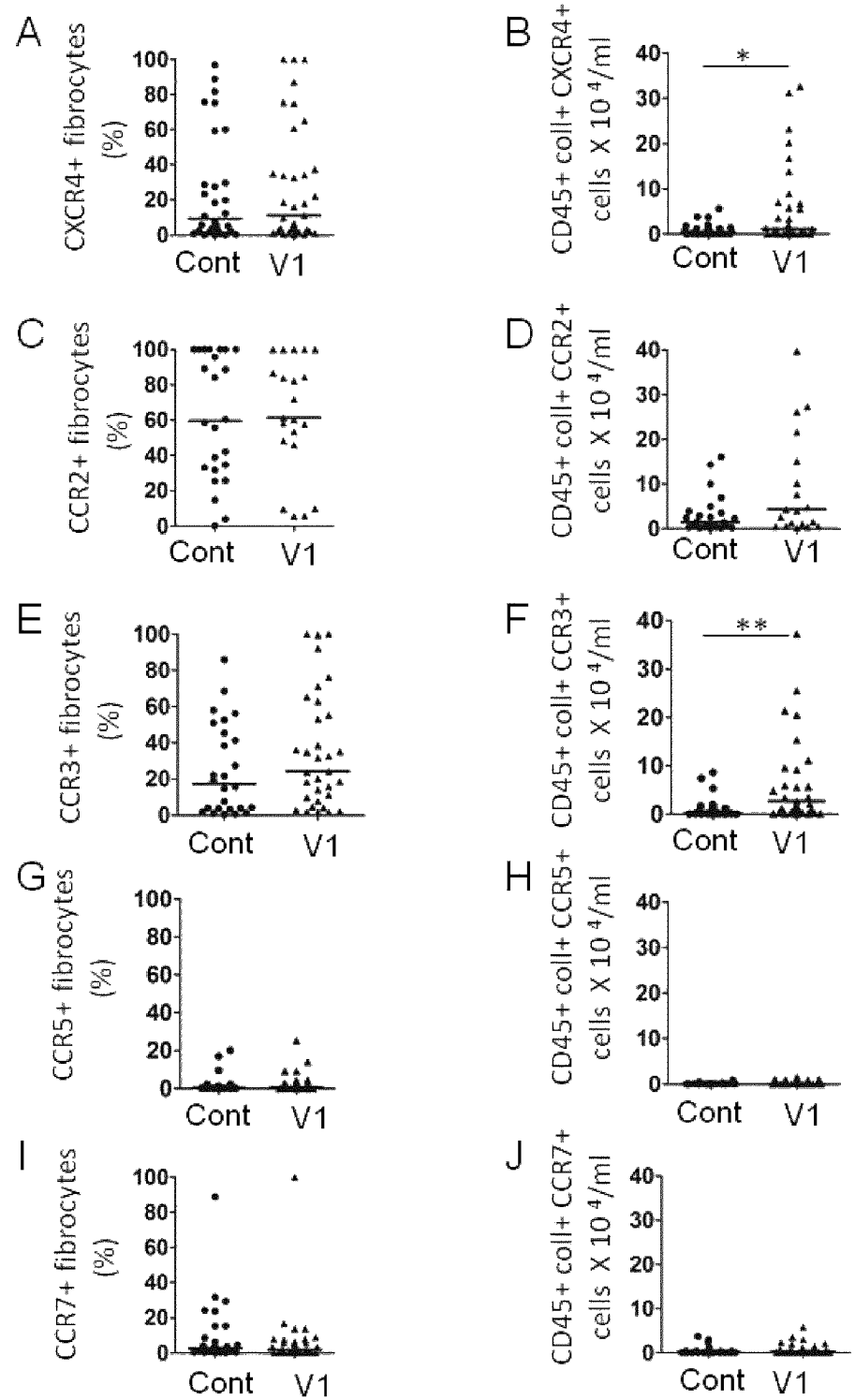
FIGS. 4 A-J are graphs showing the percentage of cells expressing CXCR4 (A), CCR2 (C), CCR3 (E), CCR5 (G) and CCR7 (I) in fibrocytes of control subjects ("Cont"), exacerbating COPD patients ("V1"). Concentration of CXCR4+ (B), CCR2+ (D), CCR3+(F), CCR5+ (H) or CCR7+ (J) fibrocytes in the blood of control subjects, non-exacerbating COPD patients, exacerbating COPD patients. *: P<0.05, *** P<0.001, Mann Whitney test.

The expression of chemokine receptors was further evaluated in fibrocytes by flow cytometry. CXCR4, CCR2 and CCR3 were expressed by a high proportion of fibrocytes (FIGS. 4A, C, E), whereas CCR5 and CCR7 were only found on a small proportion of CD45+ColI+ cells (FIGS. 4G and H). There was a higher level of CXCR4+ and CCR3+ fibrocytes in COPD patients than in control subjects (FIGS. 4B, D and F).

Role of the CXCL12/CXCR4 and CCL11/CCR3 Axes in Fibrocyte Migration

Figure 5:
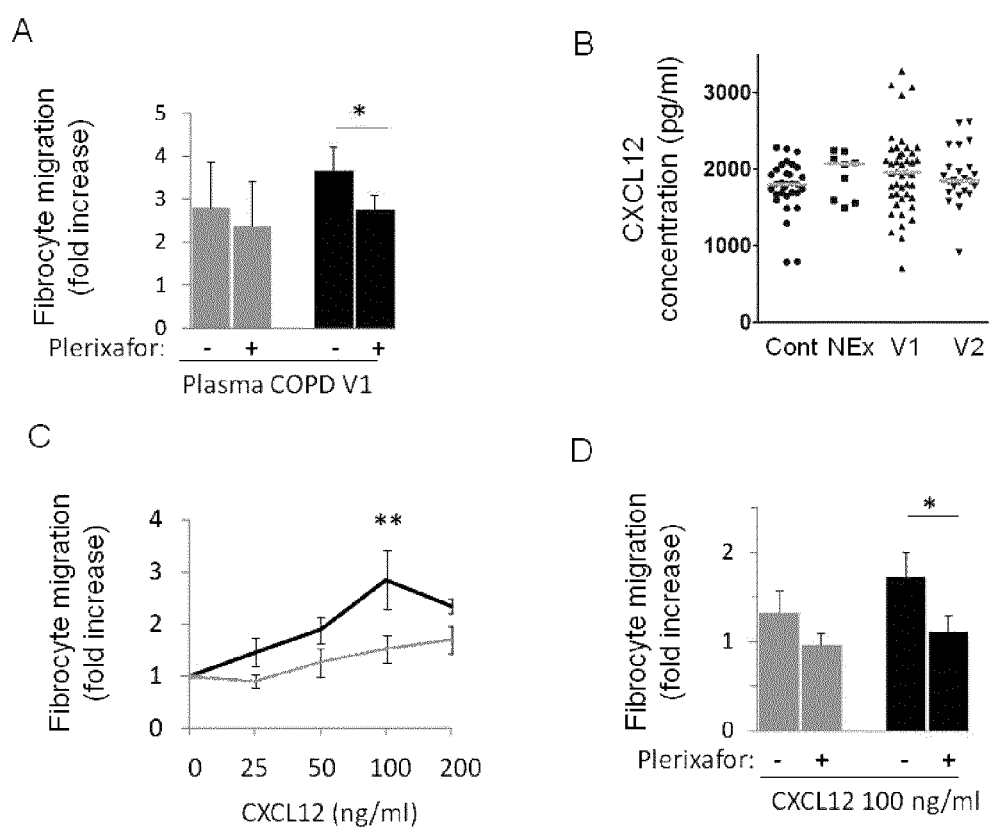
FIGS. 5A-D show A) the fibrocyte migration of control subjects (n=6, gray bars) and exacerbating COPD patients (n=6, black bars) in response to plasma of exacerbating COPD patients in presence (+) or absence (−) of 25 μg/ml Plerixafor. * P<0.05, paired t-test. B) Plasma CXCL12 in individual subjects. Symbols indicate individual subjects and horizontal lines represent medians. C) Fibrocyte migration of control subjects (n=8, gray bars) and exacerbating COPD patients (n=5, black bars) in response to CXCL12. ** P<0.01, two-way ANOVA with Bonferroni post-tests. D) Fibrocyte migration of control patients (n=6; gray bars) and exacerbating COPD patients (n=7; black bars) in response to CXCL12 in presence (+) or absence (−) of 25 μg/ml Plerixafor. *: P<0.05, paired t-test.
Figure 6:
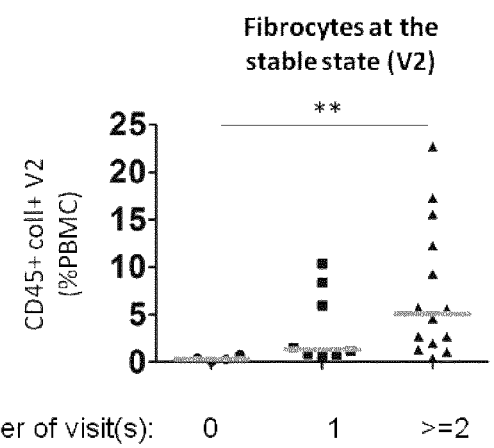
FIG. 6 is a graph showing the percentage of CD45+ Coll+ cells in PBMC of exacerbating COPD patients at V2 without any unscheduled visit (n=4), with one unscheduled visit (n=8), or with two or more unscheduled visit (n=14) the year before V1. Medians are represented as gray horizontal lines. **: p<0.01, non-parametric Kruskal Wallis test with multiple z tests.
Figure 7:
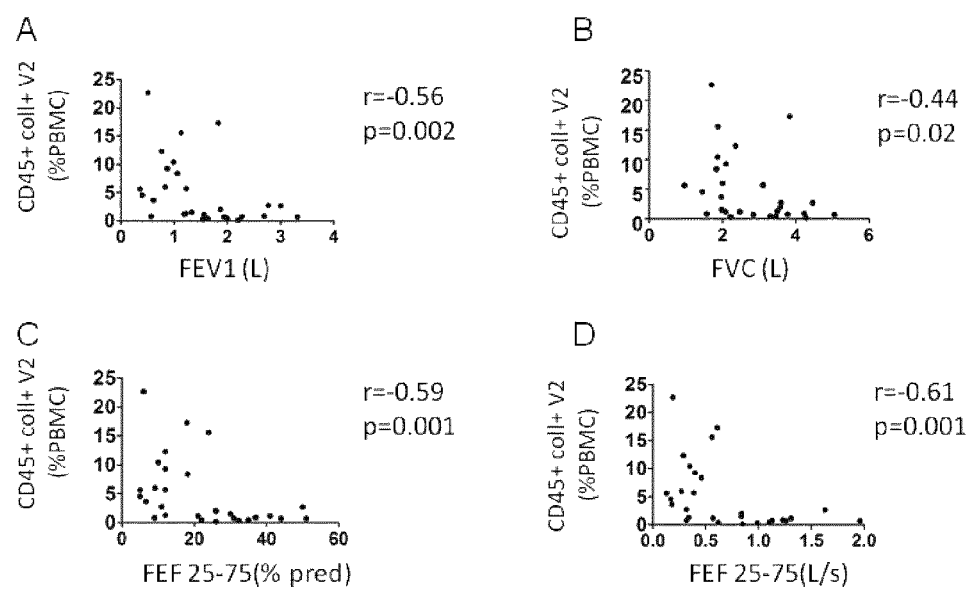
FIG. 7 shows the relationships between FEV1 (L) (A), FVC (L) (B), FEF 25-75(%) (C), FEF 25-75 (L/s) (D) and the percentage of CD45+ Coll+ cells in PBMC in exacerbating COPD patients at V2.
FEV1: Forced Expiratory Volume in the 1st second; FVC: forced vital capacity; FEF 25-75: the average forced expiratory flow during the mid (25-75%) portion of the FVC. Correlation coefficient (r) and significance level (p values) were obtained using non parametric Spearman analyses.
Figure 8:
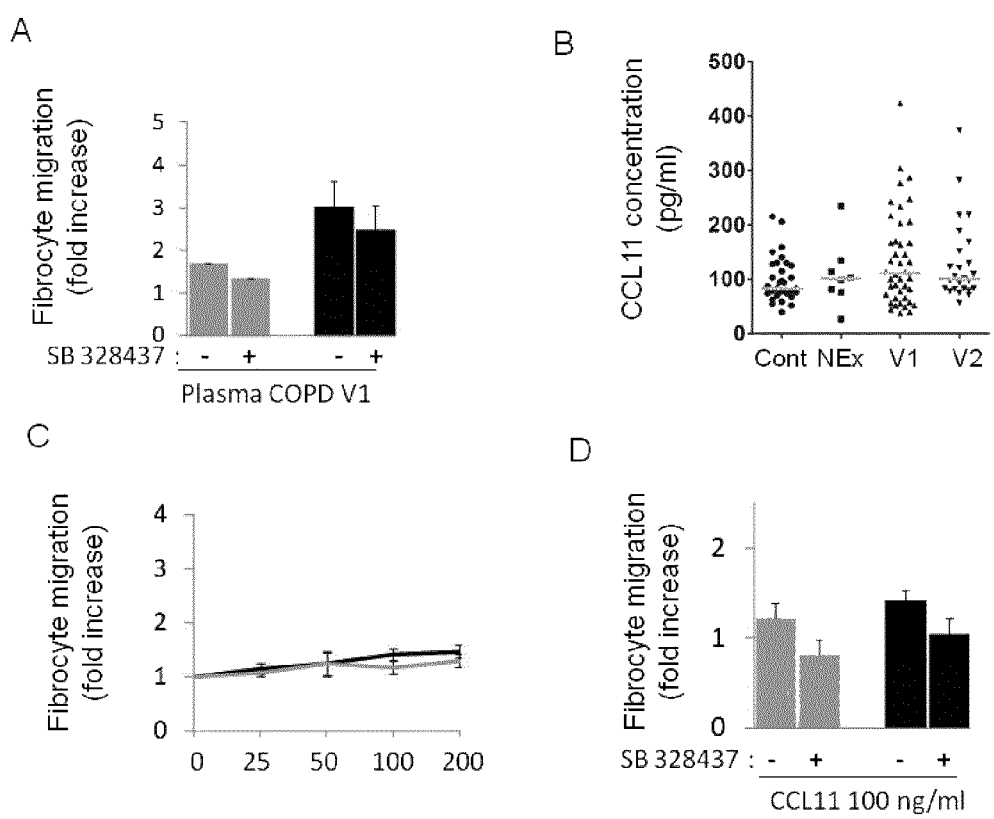
FIGS. 8 A-D are graphs showing in (A) fibrocyte migration of control subjects (n=1, gray bars) and exacerbating COPD patients (n=5, black bars) in response to plasma of exacerbating COPD patients in presence (+) or absence (−) of 10 μM SB 328437. (B) Plasma CCL11 in individual subjects. Symbols indicate individual subjects and horizontal lines represent medians. (C) Fibrocyte migration of control subjects (n=2, gray bars) and exacerbating COPD patients (n=6, black bars) in response to CCL11. (D) Fibrocyte migration of control patients (n=2) and exacerbating COPD patients (n=5) in response to CCL11 in presence (+) or absence (−) of 10 μM SB 328437.

Since more CXCR4+ and CCR3+ fibrocytes were found in the blood of exacerbating COPD patients, role of both CXCR4 and CCR3 in plasma-induced fibrocytes migration was investigated in an in vitro assay. Plerixafor, an antagonist of CXCR4 (De Clercq, E. 2003. The bicyclam AMD3100 story. *Nat Rev Drug Discov* 2(7):581-7) induced a significant reduction in the plasma-induced recruitment of fibrocytes obtained from exacerbating COPD patients but no significant reduction in the migration of fibrocytes obtained from normal subjects (FIG. 5A). By contrast, plasma-induced migration of fibrocytes from exacerbating COPD patients or from control subjects was not affected by SB 328437, an antagonist of CCR3 (White, J. R., et al. 2000. *J Biol Chem* 275(47):36626-31) (Figure E3A). Plasma concentrations of some of ligands of CXCR4 and CCR3 were also compared. Plasma concentrations of CXCL12 alpha (ligand of CXCR4) and CCL11 and CCL13 (ligands of CCR3) did not differ significantly between groups (FIG. 5B, Figure E3B). Therefore, the migratory response of fibrocytes to increasing concentrations of CXCL12 alpha and CCL11 was examined. CXCL12 alpha (FIG. 5C) but not CCL11 (Figure E3C) induced a significant fibrocytes migration in a dose-dependent manner. Interestingly, 100 ng/ml of CXCL12 alpha triggered a significantly higher migration of fibrocytes from exacerbating COPD patient compared to fibrocytes from control subjects (FIG. 5C), suggesting that fibrocytes from exacerbating COPD patient had an enhanced chemosensitivity to CXCL12 compared to fibrocytes from controls. This response was completely abolished by a treatment with plerixafor, showing that this answer was completely mediated by CXCR4 (FIG. 5D).

Example 9—Effects of the Composition and Methods of Use According to the Invention on a COPD Mouse Model A mouse model exposed to cigarette smoke (CS) combined with viral exacerbations. Said viral exacerbations were provoked by injecting a double stranded RNA inducing responses similar to these induced by viral infections, namely a poly(I:C).

Figure 9:
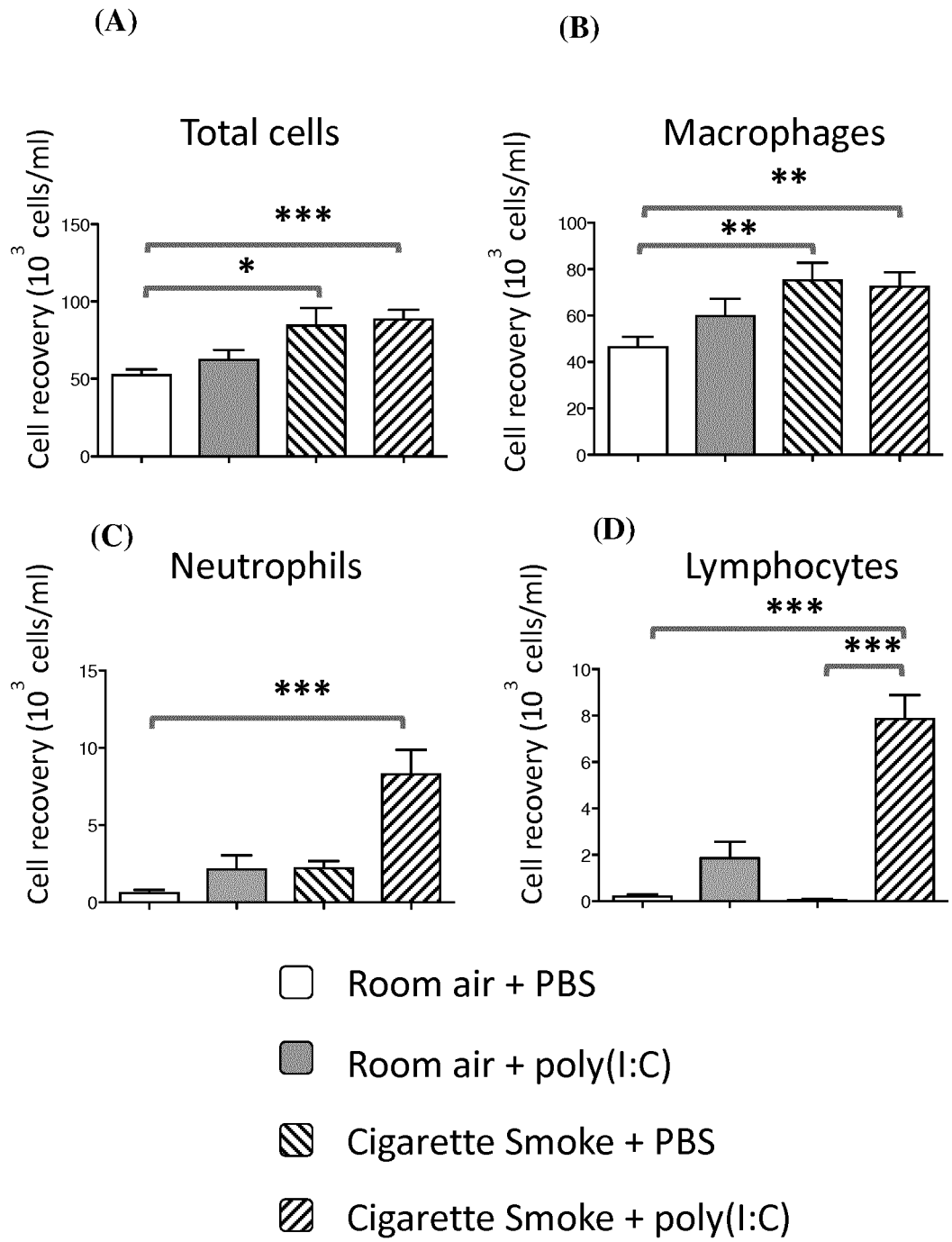
FIG. 9 are graphs showing the cell recovery ($10^3$/ml) after a bronchoalveolar lavage (BAL) with in particular (A) the total number of cell, (B) the macrophage cells recovery, (C) the neutrophils recovery, and (D) the lymphocyte recovery in each group of mice: mice exposed to room air and injected with PBS (□), mice exposed to room air and having received the double stranded RNA poly(I:C) (▩) mice exposed to cigarette smoke and injected with PBS ( ▨ ), mice exposed to cigarette smoke and injected with double stranded RNA poly(I:C) ( ▨ ).

Mice were exposed to cigarette smoke (CS) or room air (RA) during 5 weeks. The last 2 weeks of the protocol, a poly(I:C) or the vehicle (PBS) was injected twice a week. As showed in FIG. 9, CS and poly(I:C) exposure caused a modest increase in bronchoalveolar lavage (BAL) total cell and macrophage recovery. However, a substantial increase in neutrophil and lymphocyte recovery was observed (FIG. 9).

Figure 10:
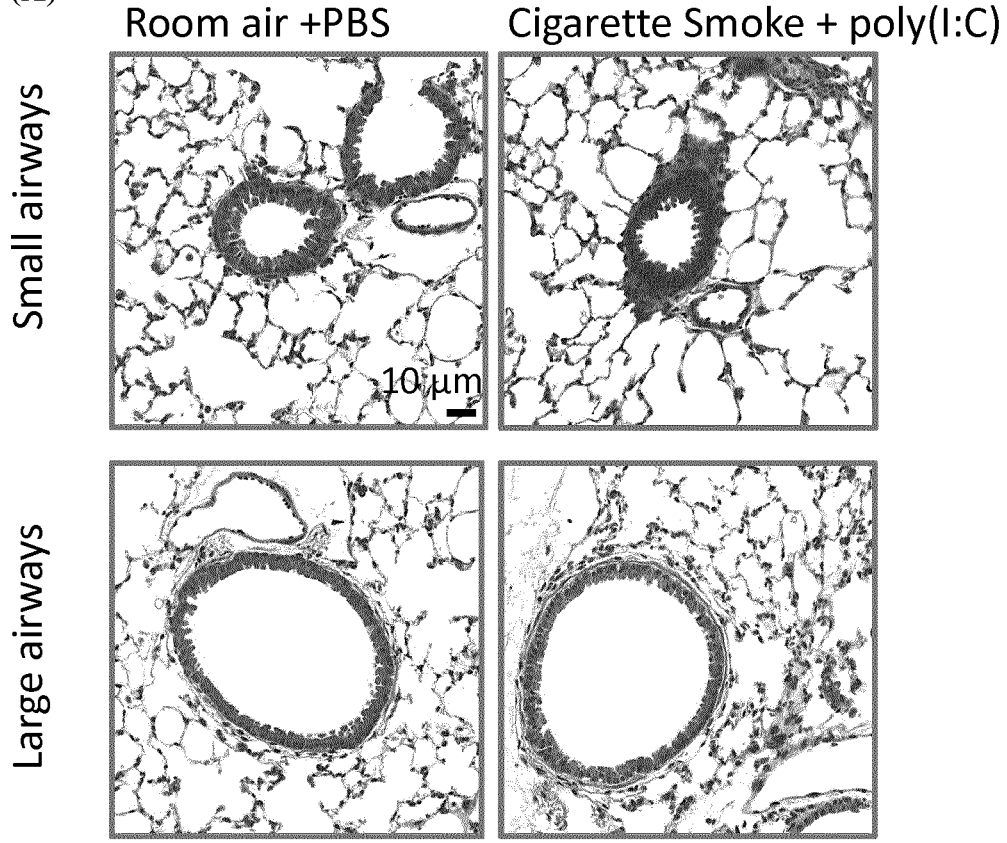
FIG. 10 (A) are electronic microscopic images from bronchial sections obtained from a group of mice exposed to cigarette smoke and injected with poly(I:C), versus a control group exposed to room air and injected with poly(I:C). (B) are graphs showing the ratio of the fibrosed area (FA) and basal lamina perimeter (PLB) in each groups of mice in each group of mice as described above in FIG. 9.
Figure 10:
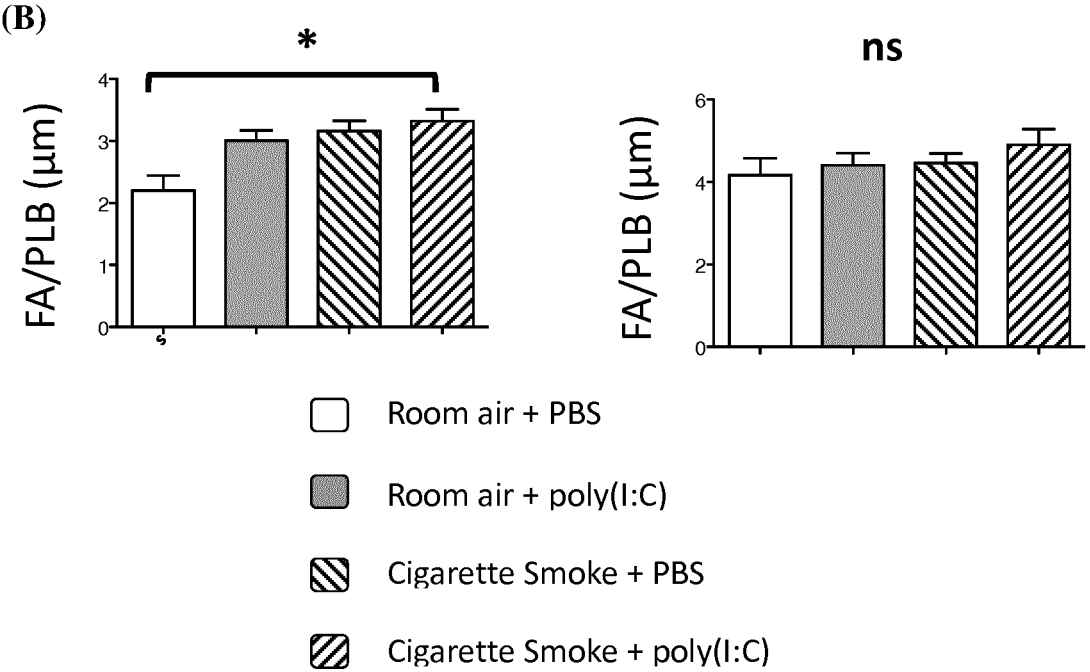

Also, an analysis of electronic microscopic images from bronchial sections obtained from mice exposed to CS and poly(I:C) versus to control mice exposed to room air and PBS demonstrated that CS and poly(I:C) induced small but not large airway fibrosis (FIG. 10A). Thus, the combination of CS and poly(I:C) produces an inflammation of the bronchial airways and structural changes characteristic to the COPD disease. An increase of the inflammation of the bronchial airways as well as an increase of peribronchial fibrosis as observed in COPD patients has been clearly showed in FIG. 10B.

Figure 11:
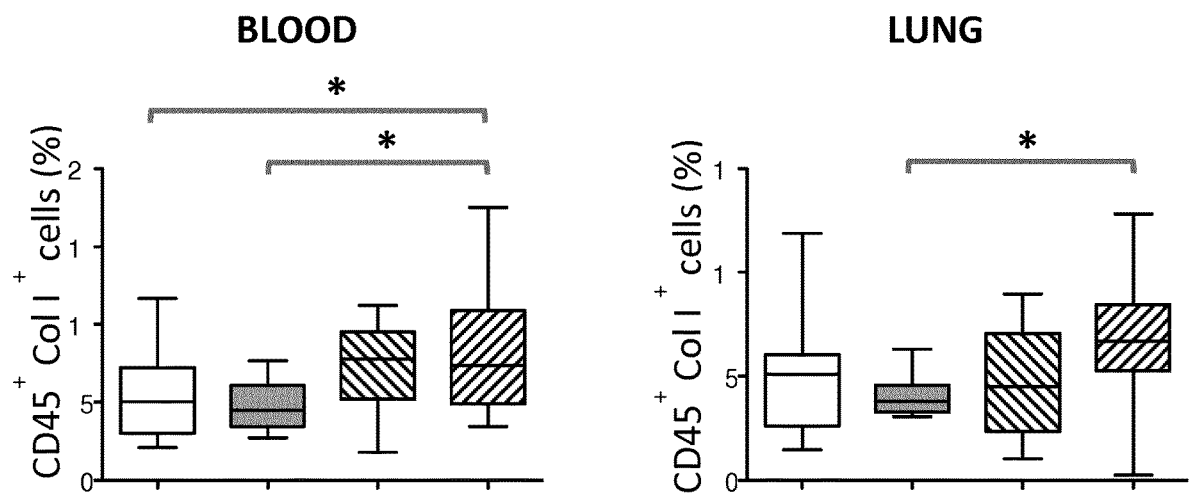
FIG. 11 shows graphs showing the percentage of circulating fibrocytes (CD45+ Coll+ cells) in blood and lung for each groups of mice in each group of mice as described above in FIG. 9.
Figure 12:
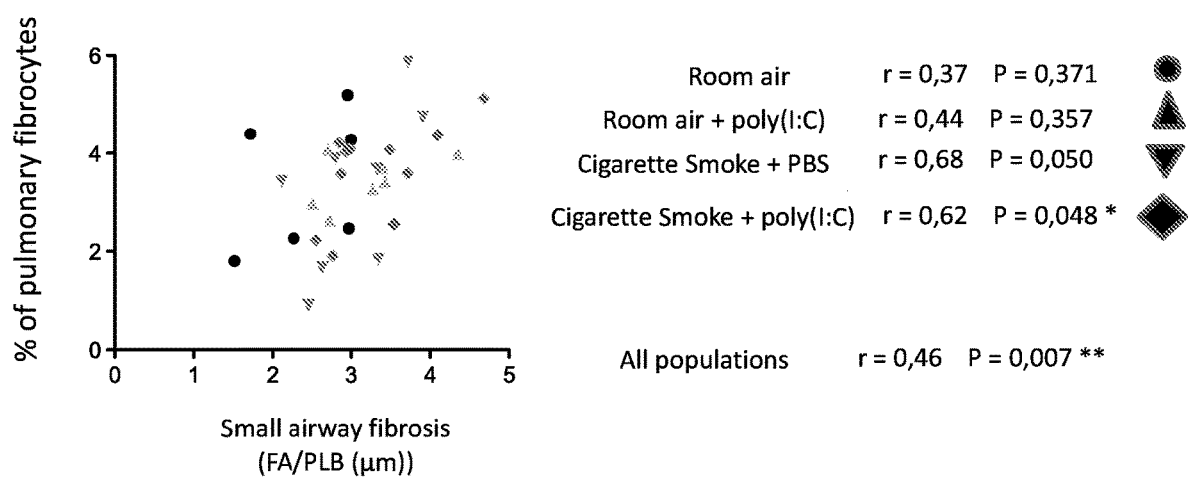
FIG. 12 is a graph showing the percentage of lung fibrocytes (CD45+ Coll+ cells) in lungs for each group of mice as described above in FIG. 9.

Furthermore, an increase of the percentage of circulating fibrocytes ("BLOOD", FIG. 11) and lung fibrocytes ("LUNG", FIG. 11) has been demonstrated in mice exposed to both cigarette smoke and poly(I:C). Interestingly, the percentage of lung fibrocytes was correlated with small airway fibrosis (FIG. 12), suggesting a role of fibrocytes in this pathophysiological process. Altogether, these data confirm the results obtained in COPD patients and add significant information on the recruitment of fibrocytes into the lung where they could play a crucial role in peribronchial fibrosis.

The invention claimed is:

1. A method of treating chronic obstructive pulmonary disease (COPD) and acute exacerbations of chronic obstructive pulmonary disease (AECOPDs) in a patient in need thereof comprising administering to said patient at least one antagonist or inhibitor of chemokine receptor CXCR4, and isoforms thereof in an amount sufficient to treat said COPD and AECOPDs, wherein the COPD and AECOPDs are characterized by bronchial and/or peribronchial fibrosis.

2. The method according to claim 1, wherein said antagonist or inhibitor is selected from a group consisting of small organic or synthetic molecules, natural products, synthetic compounds, antibodies and nucleic acids.

3. The method according to claim 1, wherein said CXCR4 antagonist is Plerixafor.

4. The method according to claim 1, wherein the antagonist or inhibitor of CXCR4 inhibits binding of CXCL12 ligand to CXCR4.

5. The method according to claim 1, wherein the antagonist or inhibitor of CXCR4 inhibits binding of CXCL12-α ligand to CXCR4.

6. The method of claim 1, further comprising administering to said patient at least one of a bronchodilator, a corticoid, and a phosphodiesterase inhibitor.

7. The method of claim 1, wherein said at least one antagonist or inhibitor is administered via an oral, buccal, or sublingual route.

8. The method of claim 1, wherein said at least one antagonist or inhibitor is in the form of tablets, capsules, soft gel capsules, multiparticulates, gels, films, elixirs, solutions or suspensions, which may contain flavoring or coloring agents, for immediate-, delayed-, sustained-, dual-, controlled-release or pulsatile delivery applications.

9. The method of claim 1, wherein said at least one antagonist or inhibitor is administered via inhalation and is in the form of a dry powder inhaler or an aerosol spray presentation from a pressurized container, pump, spray or nebuliser.

10. The method according to claim 1, wherein said CXCR4 antagonist is not Plerixafor.

11. A method of treating chronic obstructive pulmonary disease (COPD) and optionally acute exacerbations of chronic obstructive pulmonary disease (AECOPDs) in a patient in need thereof consisting of administering to said patient a therapeutically effective amount of at least one antagonist or inhibitor of chemokine receptor CXCR4 and isoforms thereof, and optionally administering to said patient a therapeutically effective amount of at least one of a bronchodilator, a corticoid, a phosphodiesterase inhibitor, or an antagonist or inhibitor of a chemokine receptor other than CXCR4, wherein the COPD and AECOPDs are characterized by bronchial and/or peribronchial fibrosis.

\* \* \* \* \*